(12) United States Patent
Elokdah et al.

(10) Patent No.: US 7,101,903 B2
(45) Date of Patent: Sep. 5, 2006

(54) SUBSTITUTED DIHYDROPYRANO INDOLE-3,4-DIONE DERIVATIVES AS INHIBITIORS OF PLASMINOGEN ACTIVATOR INHIBITOR-1 (PAI-1)

(75) Inventors: Hassan Mahmoud Elokdah, Yardley, PA (US); David Zenan Li, Princeton, NJ (US)

(73) Assignee: Wyeth, Madison, NJ (US)

( * ) Notice: Subject to any disclaimer, the term of this patent is extended or adjusted under 35 U.S.C. 154(b) by 362 days.

(21) Appl. No.: 10/731,290

(22) Filed: Dec. 9, 2003

(65) Prior Publication Data

US 2005/0113436 A1    May 26, 2005

Related U.S. Application Data

(60) Provisional application No. 60/432,327, filed on Dec. 10, 2002.

(51) Int. Cl.
*A61K 31/407*    (2006.01)
*C07D 209/56*    (2006.01)

(52) U.S. Cl. .................... 514/411; 548/427; 548/430
(58) Field of Classification Search .......... 548/427, 548/430; 514/411
See application file for complete search history.

(56) References Cited

U.S. PATENT DOCUMENTS

| | | | | |
|---|---|---|---|---|
| 3,026,325 A | 3/1962 | Heinzelman et al. | ........ | 548/496 |
| 3,476,770 A | 11/1969 | Scherrer | ................... | 548/494 |
| 3,557,142 A | 1/1971 | Bell | ...................... | 548/516 |
| 3,843,683 A | 10/1974 | Bell | ...................... | 548/493 |
| 4,478,819 A | 10/1984 | Hercelin et al. | ............ | 424/457 |
| 4,736,043 A | 4/1988 | Michel et al. | .............. | 548/492 |
| 4,851,406 A | 7/1989 | Mertens et al. | | |
| 5,164,372 A | 11/1992 | Matsuo et al. | ............... | 514/19 |
| 5,420,289 A | 5/1995 | Musser et al. | ............. | 548/159 |
| 5,482,960 A | 1/1996 | Berryman | ................. | 514/414 |
| 5,502,187 A | 3/1996 | Ayer et al. | .................. | 544/117 |
| 5,541,343 A | 7/1996 | Himmelsbach et al. | ..... | 514/424 |
| 5,612,360 A | 3/1997 | Boyd et al. | ................ | 514/381 |
| 5,859,044 A | 1/1999 | Dow et al. | ................ | 514/419 |
| 6,048,875 A | 4/2000 | De Nanteuil et al. | ........ | 514/314 |
| 6,110,963 A | 8/2000 | Malamas | ................... | 514/443 |
| 6,166,069 A | 12/2000 | Malamas et al. | .......... | 514/469 |
| 6,232,322 B1 | 5/2001 | Malamas et al. | ........... | 514/303 |
| 6,251,936 B1 | 6/2001 | Wrobel et al. | ............. | 514/443 |
| 6,302,837 B1 | 10/2001 | De Nanteuil et al. | | |
| 6,479,524 B1 | 11/2002 | Priepke et al. | ............. | 514/352 |
| 6,599,929 B1 | 7/2003 | Cho et al. | .................. | 514/415 |
| 6,787,556 B1 | 9/2004 | Hargreaves et al. | ........ | 514/311 |
| 6,800,645 B1 | 10/2004 | Cox et al. | .................. | 514/314 |
| 6,800,654 B1 | 10/2004 | Mayer et al. | .............. | 514/381 |
| 6,844,358 B1 | 1/2005 | Malamas et al. | ........... | 514/336 |
| 2003/0013732 A1 | 1/2003 | Elokdah | ..................... | 514/301 |
| 2003/0018067 A1 | 1/2003 | Elokdah et al. | ............. | 514/469 |
| 2003/0060497 A1 | 3/2003 | Gerlach | ..................... | 514/414 |
| 2003/0125371 A1 | 7/2003 | Elokdah et al. | ............. | 514/419 |
| 2004/0116488 A1 | 6/2004 | Jennings et al. | ............ | 514/374 |
| 2004/0116504 A1 | 6/2004 | Elokdah et al. | ............. | 514/419 |
| 2004/0122070 A1 | 6/2004 | Jennings | ..................... | 514/374 |
| 2004/0138283 A1 | 7/2004 | Jennings et al. | ............ | 514/414 |
| 2004/0204417 A1 | 10/2004 | Perez et al. | .................. | 514/249 |
| 2005/0070584 A1 | 3/2005 | Havran et al. | .............. | 514/357 |

(Continued)

FOREIGN PATENT DOCUMENTS

DE    3147276 A1    6/1983

(Continued)

OTHER PUBLICATIONS

J. Med. Chem, vol. 40, No. 23, 3712-3714, Hipskind, P. A., et al. (1997).

(Continued)

*Primary Examiner*—Golam M. M. Shameem
(74) *Attorney, Agent, or Firm*—Woodcock Washburn LLP

(57) ABSTRACT

Compounds of formula (I) and II) are provided

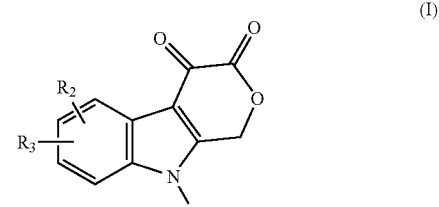

(I)

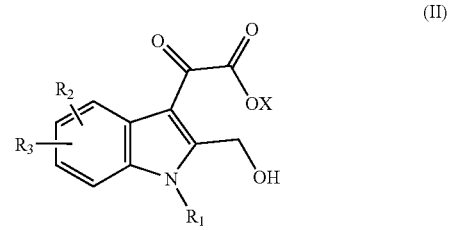

(II)

wherein: X is an alkali metal or a basic amine moiety; $R_1$ is alkyl, cycloalkyl, —$CH_2$-cycloalkyl, pyridinyl, —$CH_2$-pyridinyl, phenyl or benzyl, the rings of these groups being optionally substituted; $R_2$ is H, halogen, alkyl, perfluoroalkyl, alkoxy, cycloalkyl, —$CH_2$-cycloalkyl, —$NH_2$, or —$NO_2$; $R_3$ is phenyl, benzyl, benzyloxy, pyridinyl, or —$CH_2$-pyridinyl, with the rings of these groups being optionally substituted; or a pharmaceutically acceptable salt or ester form thereof, as well as pharmaceutical compositions and methods using these compounds as inhibitors of plasminogen activator inhibitor-1 (PAI-1) and as therapeutic compositions for treating conditions resulting from fibrinolytic disorders such as deep vein thrombosis and coronary heart disease, and pulmonary fibrosis.

19 Claims, No Drawings

U.S. PATENT DOCUMENTS

| | | | |
|---|---|---|---|
| 2005/0070585 A1 | 3/2005 | Elokdah et al. | 514/364 |
| 2005/0070587 A1 | 3/2005 | Elokdah et al. | 514/381 |
| 2005/0070592 A1 | 3/2005 | Gundersen | 514/415 |
| 2005/0096377 A1 | 5/2005 | Hu | 514/419 |
| 2005/0113428 A1 | 5/2005 | Gopalsamy et al. | 514/364 |
| 2005/0113438 A1 | 5/2005 | Hu et al. | 514/414 |
| 2005/0113439 A1 | 5/2005 | Hu | 514/414 |
| 2005/0119296 A1 | 6/2005 | Elokdah et al. | 514/300 |
| 2005/0119326 A1 | 6/2005 | Havran et al. | 514/414 |
| 2005/0119327 A1 | 6/2005 | Hu | 514/414 |
| 2005/0215626 A1 | 9/2005 | Havran et al. | 514/469 |

FOREIGN PATENT DOCUMENTS

| | | |
|---|---|---|
| DE | 43 38 770 A1 | 5/1995 |
| DE | 19543639 A1 | 5/1997 |
| DE | 19753522 | 6/1999 |
| EP | 0 416 609 A2 | 3/1991 |
| EP | 0 508 723 A1 | 10/1992 |
| EP | 0 512 570 A1 | 11/1992 |
| EP | 0 540 956 A1 | 5/1993 |
| EP | 0 655 439 A2 | 5/1995 |
| EP | 0 759 434 A1 | 2/1997 |
| EP | 0 819 686 A1 | 1/1998 |
| EP | 0 822 185 A1 | 2/1998 |
| EP | 0 955 299 A1 | 11/1999 |
| EP | 1 092 716 | 4/2001 |
| EP | 1 156 045 | 11/2001 |
| FR | 2 244 499 A1 | 4/1975 |
| FR | 2 777 886 A1 | 10/1999 |
| FR | 2 799 756 A1 | 4/2001 |
| GB | 1 321 433 | 6/1973 |
| WO | 94/13637 A1 | 6/1994 |
| WO | 94/14434 A1 | 7/1994 |
| WO | 94/26738 A1 | 11/1994 |
| WO | 95/10513 A1 | 4/1995 |
| WO | 96/06840 A1 | 3/1996 |
| WO | 96/21656 A1 | 7/1996 |
| WO | 96/26207 A1 | 8/1996 |
| WO | WO 96/32379 | 10/1996 |
| WO | 97/09308 A1 | 3/1997 |
| WO | 97/43260 A1 | 11/1997 |
| WO | 97/48697 A1 | 12/1997 |
| WO | 98/08818 A1 | 3/1998 |
| WO | WO 99/28297 | 6/1999 |
| WO | 99/43672 A1 | 9/1999 |
| WO | 99/46260 A1 | 9/1999 |
| WO | WO 99/43651 | 9/1999 |
| WO | WO 99/43654 | 9/1999 |
| WO | 99/50268 A1 | 10/1999 |
| WO | 99/58519 A1 | 11/1999 |
| WO | 99/61435 A1 | 12/1999 |
| WO | 00/32180 A2 | 6/2000 |
| WO | 00/35919 A1 | 6/2000 |
| WO | 00/46195 A1 | 8/2000 |
| WO | 00/046197 A1 | 8/2000 |
| WO | 00/64876 A1 | 11/2000 |
| WO | 00/64888 A1 | 11/2000 |
| WO | 01/12187 A2 | 2/2001 |
| WO | 02/030895 A1 | 4/2002 |
| WO | 02/072549 A1 | 9/2002 |
| WO | 03/000253 A1 | 1/2003 |
| WO | WO 03/000253 A1 | 1/2003 |
| WO | 03/031409 A1 | 4/2003 |
| WO | 03/068742 A1 | 8/2003 |
| WO | 03/087087 A2 | 10/2003 |
| WO | 2004/052854 A2 | 6/2004 |

OTHER PUBLICATIONS

Chitra Krishnamurti et al., Blood, Mar. 1987, 798-803, 69(3).
Christopher F. Reilly et al., Arteriosclerosis and Thrombosis, Sep./Oct. 1991, 1276-1286, 11(5).
Peter Carmeliet et al., J. Clin. Investigations, 1993, 2756-2760, 92.
E. Rocha et al., Fibrinolysis, 1994, 294-303, 8.
Justo Aznar et al., Haemostasis, 1994, 243-251, 24.
B.J. Biemond et al., Circulation, 1995, 1175-1181, 91(4).
Marcel Levi et al., Circulation, Jan. 1992, 305-312, 85(1).
Thomas K. Nordt et al., J. Clin. Endocrinology and Metabolism, 2000, 1563-1568, 85(4).
E. Daci et al., J. Bone and Mineral Research, 2000, 1510-1516, 15(8).
Crandall, D. L. et al., "Characterization and comparative evaluation of a structurally unique PAI-1 inhibitor exhibiting oral in-vivo efficacy," *Journal of Thrombosis and Haemostasis*, Mar. 17, 2004, 2: 1422-1428.
Guzzo, P.R. et al., "Synthesis of a conformationally constrained threonin-valine dipeptide mimetic: design of a potential inhibitor of plasminogen activator inhibitor-1," Tetrahedron Letters, *Tetrahedron Letters*, 43(1), 41-43 (2002).
Charlton, Peter, "The status of plasminogen activator inhibitor-1 as a therapeutic target," Expert *Opinion On Investigational Drugs*, (May 1997), vol. 6, No. 5, pp. 539-554.
Malamas, M.S. et al. "Characterization and comparative evaluation of a structurally unique PAI-1 inhibitor exhibiting oral in-vivo efficacy," *Journal of Medicinal Chemistry*, 43(7):1293-1310, 2000.
Da Settimo, A. et al., "Reaction of indole derivatives with bromine, substitution, oxidation, and dimerization," *J Org Chem*, 1970, 35(8):2546-2551.
U.S. Appl. No. 10/947,710, filed Sep. 23, 2004, Commons et al.
U.S. Appl. No. 10/947,711, filed Sep. 23, 2004, Gopalsamy et al.
U.S. Appl. No. 11/208,777, filed Aug. 22, 2005, Commons et al.
U.S. Appl. No. 11/208,772, filed Aug. 22, 2005, Commons.
U.S. Appl. No. 11/208,775, filed Aug. 22, 2005, Commons et al.
Aggarwal et al., "A catalytic antibody programmed for torsional activation of amide bond hydrolysis," *Chem. Eur. J.*, Jan. 25, 2003, 9(13), 3132-3142.
Ballantine, J. A., "The Chemistry of Bacteria," *Journal of the Chemical Society Abstracts*, 1957, 2222-2227.
Delgado et al., Journal of Organic Chemistry (1993), 58(10), pp. 2862-2866.
Dillard R. D. et al., "Indole Inhibitors of Human Nonpancreatic Secretory Phospholipase $A_2$ 1. Indole-3-Acetamides", *Journal of Medicinal Chemistry*, American Chemical Society, 39(26), 5119-5136, 1996.
Hipskind, P. A. et al., "Potent and selective 1,2,3-trisubstituted indole NPY Y-1 antagonists," *J Med Chem*, 1997, 40(23), 3712-3714.
Julia et al., CA 57:49169, 1962.
Malamas, M. S. et al., "Antihyperglycemic activity of new 1,2,4-oxadiazolidine-3,5-diones," *Eur. J. Med. Chem.*, 2001, 36, 31-42.
Malamas, M.S. et al. "Novel benzofuran and benzothiophene biphenyls as inhibitors of protein tyrosine phosphatase 1B with antihyperglycemic properties," *Journal of Medicinal Chemistry*, Apr. 6, 2000, 43(7), 1293-1310.
Moody et al., CA 120:298300, 1994.
Shengeliya, M. S. et al., "N-Glycosides of 5-amino-2-(ethoxycarbonyl)indole," *Zhurnal Organicheskoi Khimii*, 1986, 22(9), 1868-1873.

SUBSTITUTED DIHYDROPYRANO INDOLE-3,4-DIONE DERIVATIVES AS INHIBITIORS OF PLASMINOGEN ACTIVATOR INHIBITOR-1 (PAI-1)

This application claims priority from co-pending provisional application Ser. No. 60/432,327 filed on Dec. 10, 2002, the entire disclosure of which is hereby incorporated by reference.

This invention relates to substituted dihydropyrano indole-3,4-dione derivatives useful as inhibitors of plasminogen activator inhibitor-1 (PAI-1) and therapeutic compositions containing such compounds for treating conditions resulting from fibrinolytic disorders such as deep vein thrombosis and coronary heart disease, and pulmonary fibrosis.

BACKGROUND OF INVENTION

Plasminogen activator inhibitor-1 (PAI-1) is a major regulatory component of the plasminogen-plasmin system. PAI-1 is the principal physiologic inhibitor of both tissue type plasminogen activator (tPA) and urokinase type plasminogen activator (uPA). Elevated plasma levels of PAI-1 have been associated with thrombotic events as indicated by animal experiments (Krishnamurti, *Blood*, 69, 798 (1987); Reilly, *Arteriosclerosis and Thrombosis*, 11, 1276 (1991); Carmeliet, *Journal of Clinical Investigation*, 92, 2756 (1993)) and clinical studies (Rocha, *Fibrinolysis*, 8, 294, 1994; Aznar, *Haemostasis* 24, 243 (1994)). Antibody neutralization of PAI-1 activity resulted in promotion of endogenous thrombolysis and reperfusion (Biemond, *Circulation*, 91, 1175 (1995); Levi, *Circulation* 85, 305, (1992)). Elevated levels of PAI-1 have also been implicated in diseases of women such as polycystic ovary syndrome (Nordt, *Journal of clinical Endocrinology and Metabolism*, 85, 4, 1563 (2000)) and bone loss induced by estrogen deficiency (Daci, *Journal of Bone and Mineral Research*, 15, 8, 1510 (2000)). Accordingly, agents that inhibit PAI-1 would be of utility in treating conditions originating from fibrinolytic disorder such as deep vein thrombosis, coronary heart disease, pulmonary fibrosis, Alzheimer's disease, polycystic ovary syndrome, etc.

WO 99/43654 and WO 99/43651 disclose indole derivatives of the following formula as inhibitors of phospholipase enzymes useful in preventing inflammatory conditions.

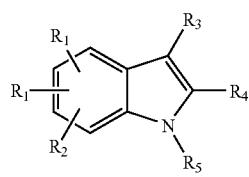

U.S. Pat. No. 4,851,406 discloses cardiotonic compounds of the following formula:

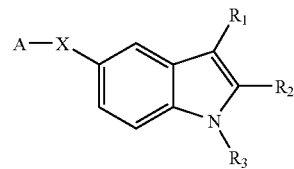

wherein: A is a five-membered, or six-membered ring heterocycle; X is a bond, an alkylene, or a vinylene radical; $R_1$ is a H, alkyl, alkenyl, cycloalkyl, cycloalkenyl, carboxyl, cyano, alkylcarbonyl, alkoxycarbonyl, aminocarbonyl, alkylaminocarbonyl, dialkylaminocarbonyl or aryl radical; $R_2$ is H, alkyl, trihalogenomethyl, hydroxyl, cycloalkyl, cyano, carboxyl, cycloalkenyl, carboxyl, cyano, alkylcarbonyl, alkoxycarbonyl, aminocarbonyl, alkylaminocarbonyl, dialkylaminocarbonyl or aryl radical; and $R_3$ is a hydrogen atom.

WO 96/32379 teaches PDE-inhibitor compounds of the following formula I:

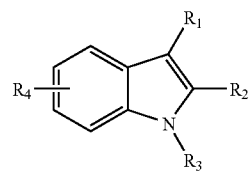

wherein $R_1$ is a H, halogen, nitro, carboxy, protected carboxy, lower alkenyl, or acyl; $R_2$ is H, halogen, carboxy, lower alkenyl, or acyl; $R_3$ is a lower alkenyl, or lower alkenyl, both optionally substituted; and $R_4$ is carboxy, protected carboxy, or acyl.

WO 9928297 relates to substituted indoles of the following formula with thrombin inhibiting effect and fibrinogen receptor antagonist effect.

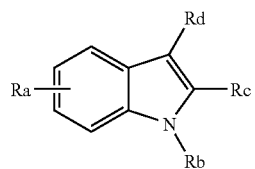

where: Ra is halogen, carboxy, $R_3R_4N$—CO—, $R_3R_4SO_2$—, or $R_4R5N$—; Rb and Rd are either alkyl or $R_2$-A where $R_2$ is a phenyl optionally substituted and A is an alkylene or a substituted alkylene; and Rc is a hydrogen, or alkyl.

EP 0 655 439 teaches 5,6 fused ring bicyclic compounds inclusive of indoles, benzofurans, and benzothiophenes corresponding the following formula as platelet aggregation inhibitors.

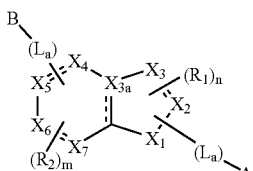

SUMMARY OF THE INVENTION

This invention is directed to compounds of formulas I and II:

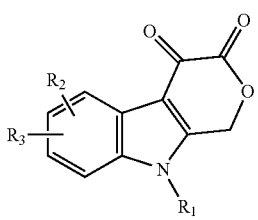

(I)

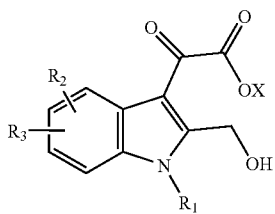

(II)

wherein:

X is hydrogen, an alkali metal or a basic amine moiety $R_1$ is $C_1$–$C_8$ alkyl, preferably $C_1$–$C_6$ alkyl, $C_3$–$C_6$ cycloalkyl, —$CH_2$—$C_3$–$C_6$ cycloalkyl, pyridinyl, —$CH_2$-pyridinyl, phenyl or benzyl, wherein the rings of the cycloalkyl, pyridinyl, phenyl and benzyl groups may be optionally substituted by, from 1 to 3 groups selected from, halogen, $C_1$–$C_6$ alkyl, $C_1$–$C_6$ perfluoroalkyl, —O—$C_1$–$C_6$ perfluoroalkyl, $C_1$–$C_6$ alkoxy, —OH, —$NH_2$, or —$NO_2$;

$R_2$ is hydrogen, halogen, $C_1$–$C_6$ alkyl, $C_1$–$C_3$ perfluoroalkyl, $C_1$–$C_6$ alkoxy, $C_3$–$C_6$ cycloalkyl, —$CH_2$—$C_3$–$C_6$ cycloalkyl, hydroxy, —$NH_2$, or —$NO_2$;

$R_3$ is hydrogen, halogen, $C_1$–$C_6$ alkyl, $C_1$–$C_3$ perfluoroalkyl, $C_1$–$C_6$, $C_3$–$C_6$ cycloalkyl, $CH_2$—$C_3$–$C_6$ cycloalkyl, hydroxy, —$NH_2$, —$NO_2$, phenyl, benzyl, benzyloxy, pyridinyl, or —$CH_2$-pyridinyl, wherein the rings of these groups may be optionally substituted by from 1 to 3 groups selected from phenyl, halogen, $C_1$–$C_6$ alkyl, $C_1$–$C_6$ perfluoroalkyl, —O—$C_1$–$C_6$ perfluoroalkyl, $C_1$–$C_6$ alkoxy, —OH, —$NH_2$, or —$NO_2$; or a pharmaceutically acceptable salt or ester form thereof.

DETAILED DESCRIPTION OF THE INVENTION

Preferred forms of the compounds of this invention are those of formulas (III) and (IV):

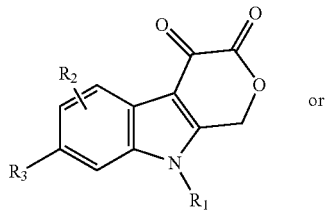

(III)

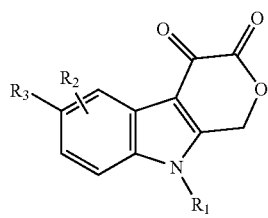

(IV)

wherein $R_1$, $R_2$, and $R_3$ are as defined above, or a pharmaceutically acceptable salt or ester form thereof.

More preferred compounds of this invention are those of formulas (V) and (VI):

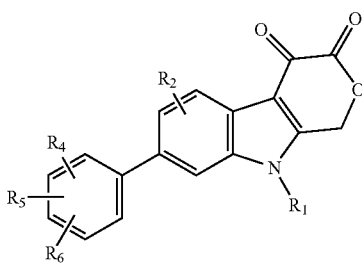

(V)

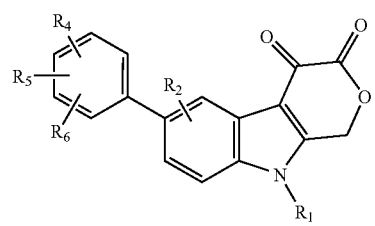

(VI)

wherein:

$R_1$ is $C_1$–$C_8$ alkyl, preferably $C_1$–$C_6$ alkyl, $C_3$–$C_6$ cycloalkyl, —$CH_2$—$C_3$–$C_6$ cycloalkyl, or benzyl, wherein the rings of the cycloalkyl and benzyl groups may be optionally substituted by from 1 to 3 groups selected from halogen, $C_1$–$C_6$ alkyl, $C_1$–$C_6$ perfluoroalkyl, —O—$C_1$–$C_6$ perfluoroalkyl, $C_1$–$C_6$ alkoxy, —OH, —$NH_2$, or —$NO_2$;

$R_2$ is hydrogen, halogen, $C_1$–$C_6$ alkyl, $C_1$–$C_3$ perfluoroalkyl, preferably —$CF_3$, $C_1$–$C_6$ alkoxy, $C_3$–$C_6$ cycloalkyl, —$CH_2$—$C_3$–$C_6$ cycloalkyl, hydroxy, —$NH_2$, or —$NO_2$;

$R_4$, $R_5$ and $R_6$ are each independently hydrogen, phenyl, halogen, $C_1$–$C_3$ alkyl, $C_1$–$C_3$ perfluoroalkyl, preferably —$CF_3$, —O—$C_1$–$C_3$ perfluoroalkyl, $C_1$–$C_3$ alkoxy, —OH, —$NH_2$, or —$NO_2$; or a pharmaceutically acceptable salt or ester form thereof.

The alkali metals suitable for use in the present invention include: sodium, potassium, lithium, calcium, magnesium, etc. The basic amine moieties include: amonia, primary amines, secondary amines, tertiary amines, pyridine, aromatic amines, benzyl amines, etc. The term "alkyl" includes both straight and branched carbon chains. The preferred $C_1$–$C_3$ perfluoroalkyl substituent is —$CF_3$ and the preferred O—$C_1$–$C_3$ perfluoroalkyl substituent is —$OCF_3$.

The present invention further comprises a method of inhibiting in a mammal plasminogen activator type 1 (PAI-I) comprising administering to a mammal in need thereof a therapeutically effective amount of a compound of formulas (I) and (II):

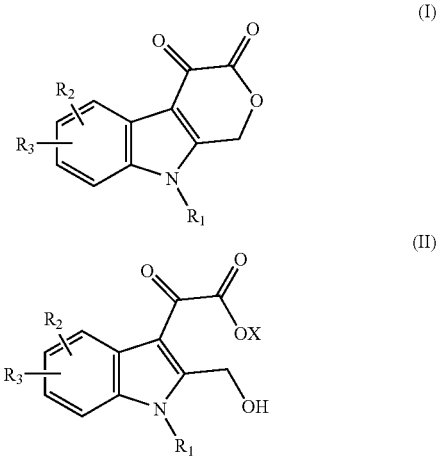

wherein:

X is hydrogen, an alkali metal or a basic amine moiety as defined above $R_1$ is $C_1$–$C_8$ alkyl, preferably $C_1$–$C_6$ alkyl, $C_3$–$C_6$ cycloalkyl, —$CH_2$—$C_3$–$C_6$ cycloalkyl, pyridinyl, —$CH_2$-pyridinyl, phenyl or benzyl, wherein the rings of the cycloalkyl, pyridinyl, phenyl and benzyl groups may be optionally substituted by, from 1 to 3 groups selected from, halogen, $C_1$–$C_6$ alkyl, $C_1$–$C_6$ perfluoroalkyl, —O—$C_1$–$C_6$ perfluoroalkyl, $C_1$–$C_6$ alkoxy, —OH, —$NH_2$, or —$NO_2$;

$R_2$ is hydrogen, halogen, $C_1$–$C_6$ alkyl, $C_1$–$C_3$ perfluoroalkyl, $C_1$–$C_6$ alkoxy, $C_3$–$C_6$ cycloalkyl, —$CH_2$—$C_3$–$C_6$ cycloalkyl, hydroxy, —$NH_2$, or —$NO_2$;

$R_3$ is hydrogen, halogen, $C_1$–$C_6$ alkyl, $C_1$–$C_3$ perfluoroalkyl, $C_1$–$C_6$, $C_3$–$C_6$ cycloalkyl I, $CH_2$—$C_3$–$C_6$ cycloalkyl, hydroxy, —$NH_2$, —$NO_2$, phenyl, benzyl, benzyloxy, pyridinyl, or —$CH_2$-pyridinyl, wherein the rings of these groups may be optionally substituted by from 1 to 3 groups selected from phenyl, halogen, $C_1$–$C_6$ alkyl, $C_1$–$C_6$ perfluoroalkyl, —O—$C_1$–$C_6$ perfluoroalkyl, $C_1$–$C_6$ alkoxy, —OH, —$NH_2$, or —$NO_2$; or a pharmaceutically acceptable salt or ester form thereof.

The preferred salt forms of the compounds herein include but are not limited to sodium salts, and potassium salts. Other useful salt forms of these compounds include those formed with pharmaceutically acceptable inorganic and organic bases known in the art. Salt forms prepared using inorganic bases include hydroxides, carbonates or bicarbonates of the therapeutically acceptable alkali metals or alkaline earth metals, such as sodium potassium, magnesium, calcium and the like. Acceptable organic bases include amines, such as benzylzmine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Also useful are alkylene diamines containing up to 6 carbon atoms, such as hexamethylenediamine; cyclic saturated or unsaturated bases containing up to 6 carbon atoms, including pyrrolidine, peperidine, morpholine, piperazine and their N-alkyl and N-hydroxyalkyl derivatives, such as N-methylmorpholine and N-(2-hyroxyethyl)-piperidine, or pyridine. Quaternary salts may also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-di-methylmorpholinium, N-methyl-N-(2-hydroxyethyl)-morpholinium, or N,N-dimethyl-piperidinium salt forms. These salt forms may be prepared using the acidic compound(s) of Formula I and procedures known in the art.

Ester forms of the compounds of this invention include straight chain alkyl esters having from 1 to 6 carbon atoms or branched chain alkyl groups containing 3 or 6 carbon atoms, including methyl, ethyl, propyl, butyl, 2-methylpropyl and 1,1-dimethylethyl esters. Other esters useful with this invention include those of the formula —$COOR_7$ wherein $R_7$ is selected from the formulae:

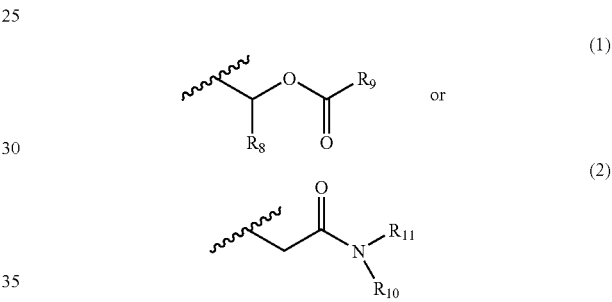

wherein $R_8$, $R_9$, $R_{10}$, $R_{11}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Among the preferred ester forms of the compounds herein include but not limited to $C_1$–$C_6$ alkyl esters, $C_3$–$C_6$ branched alkyl esters, benzyl esters, etc.

As used herein, "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryl groups include phenyl, naphthyl and the like. As used herein, "heteroaryl" refers to an aromatic heterocyclic ring system (monocyclic or bicyclic) where the heteroaryl moieties are five or six membered rings containing 1 to 4 heteroatoms selected from oxygen, nitrogen and sulfur. Such heteroaryl groups can have a single ring, such as pyridyl, pyrrolyl or furyl groups, or multiple condensed rings, such as indolyl, indolizinyl, benzofuranyl or benzothienyl groups. Preferred heteroaryls include pyridyl, pyrrolyl and furyl.

Unless otherwise limited by the definition for the aryl or heteroaryl groups herein, such groups can optionally be substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. Substituents on the alkyl, alkenyl, alkynyl, thioalkoxy and alkoxy groups mentioned above include halogens, CN, OH, and amino groups. Preferred substituents on the aryl groups herein include alkyl, alkoxy, halo, cyano, nitro, trihalomethyl, and thioalkoxy.

The compounds of the present invention are inhibitors of the serine protease inhibitor PAI-1, and are therefore useful in the treatment, inhibition, prevention or prophylaxis in a mammal, preferably in a human, of those processes which involve the production and/or action of PAI-1. Thus, the compounds of the invention are useful in the treatment or prevention of noninsulin dependent diabetes mellitus and prevention of thrombotic events associated with coronary artery and cerebrovascular disease. These compounds would also be useful for inhibiting the disease process involving the thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery (such as joint replacement), and peripheral arterial occlusion. These compounds are also useful in treating stroke associated with aor resulting from atrial fibrillation.

The compounds of the invention may also be useful in the treatment of diseases associated with extracellular matrix accumulation, including, but not limited to, renal fibrosis, chronic obstructive pulmonary disease, polycystic ovary syndrome, restenosis, renovascular disease and organ transplant rejection.

The compounds of the invention may also be useful in the treatment of malignancies, and diseases associated with neoangiogenesis (such as diabetic retinopathy).

The compounds in the invention may also be used in conjunction with and following processes or procedures involving maintaining blood vessel patency, including vascular surgery, vascular graft and stent patency, organ, tissue and cell implantation and transplantation.

The compounds of the invention may also be used in the treatment of Alzheimer's disease. This method may also be characterized as the inhibition of plasminogen activator by PAI-1 in a mammal, particularly a human, experiencing or subject to Alzhemier's disease. This method may also be characterized as a method of increasing or normalizing levels of plasmin concentration in a mammal, particularly those experiencing or subject to Alzheimer's disease.

The compounds of the present invention are useful for the treatment of blood and blood products used in dialysis, blood storage in the fluid phase, especially ex vivo platelet aggregation. The present compounds may also be added to human plasma during the analysis of blood chemistry in hospital settings to determine the fibrinolytic capacity thereof.

The compounds in the present invention may also be used in combination with prothrombolytic, fibrinolytic and anticoagulant agent.

The compounds of the present invention may also be used to treat cancer including, but not limited to, breast and ovarian cancer, and as imaging agents for the identification of metastatic cancers.

The compounds of the invention may also be useful in the treatment of myelofibrosis with myeloid metaplasia by regulating stromal cell hyperplasia and increases in extracellular matrix proteins.

The present compounds may also be used in conjunction with protease inhibitors containing highly active antiretroviral therapy (HAART) for the treatment of diseases which originate from fibrinolytic impairment and by hypercoagulability of HIV-1 infected patients receiving such therapy.

The compounds of the invention may be used for the treatment of diabetic neuropathy and renal dialysis associated with nephropathy.

The compounds of the invention may be used to treat cancer, septicemia, obesity, insulin resistance, proliferative diseases, such as psoriasis, improving coagulation homeostasis, cerebrovascular diseases, microvascular disease, hypertension, dementia, osteoporosis, arthritis, asthma, heart failure, arrhythmia, angina, as a hormone replacement agent, treating, preventing or reversing progression of atherosclerosis, Alzheimer's disease, osteopenia, reducing inflammatory markers, reducing C-reactive protein, preventing or treating low grade vascular inflammation, stroke, coronary heart disease, primary and secondary prevention of myocardial infarction, stable and unstable angina, primary prevention of cardiovascular events, secondary prevention of cardiovascular events, peripheral vascular disease, peripheral arterial disease, acute vascular syndromes, reducing the risk of undergoing a myocardial revascularization procedure, micromuscular diseases such as nephropathy, neuropathy, retinopathy, nephrotic syndrome, Type 1 and Type 2 diabetes and related diseases, hyperglycemia, hyperinsulinemia, malignant lesions, pre malignant lesions, gastro intestinal malignancies, liposarcomas and epithelial tumors, proliferative diseases such as psoriasis, improving coagulation, homeostasis and/or improving endothelial function and all forms of cerebrovascular diseases.

The compounds of the invention may also be used for topical application in wound healing for the prevention of scarring.

Methods for the treatment, inhibition, prevention or prophylaxis in a mammal of each of the conditions or maladies listed herein are part of this invention. Each method comprises administering to a mammal in need thereof a pharmaceutically or therapeutically effective amount of a compound of this invention, or a pharmaceutically acceptable salt or ester form thereof.

The compounds of the present invention can be readily prepared according to the method described in Scheme I or modification thereof using readily available starting materials, reagents and conventional synthetic procedures. It is also possible to make use of variants of these process steps, which in themselves are known to and well within the preparatory skill of the medicinal chemist. In the following reaction schemes, $R_1$, $R_2$, $R_4$, $R_5$ and $R_6$ are selected from the groups defined above.

In Scheme I, the bromo-indole-2-Carboxylates (II) were reacted with alkyl halides or aryl-alkyl halides using a base such as sodium hydride in DMF or THF to give the N-substituted bromo-indole carboxylates (III). The N-substituted bromo-indole carboxylates (III) were then subjected to palladium catalyzed cross-coupling with various substituted aryl-halides affording the N-substituted Aryl-indole carboxylates (V). Alternatively, reaction of bromo-indole-2-Carboxylates (II) with various substituted aryl-boronic acids under the palladium catalyzed cross-coupling conditions afforded the aryl-indole carboxylates (IV). Alkylation of (IV) with alkyl-halides or aryl-alkyl-halides under basic conditions as described above afforded the N-substituted Aryl-indole carboxylates (V). Reduction of V to the corresponding alcohol (VI) was accomplished by treating V with lithium aluminum hydride in ether or THF. Reaction of the alcohol (VI) with acetyl chloride in presence of a base such as triethyl amine or N,N-diisopropyl ethyl amine in an inert solvent such as methylene chloride afforded the acetate VII. Reaction of VII with oxalyl chloride in THF or dichloromethane and subsequent quenching with water furnished the keto acid VIII. Treatment of the acetate (VIII) with an aqueous base such as KOH or NaOH in a solvent such as THF furnished the carboxylate salt (IX). Lactonization of (IX) to the corresponding pyrano indole derivatives (I) was accomplished by treating IX with an aqueous acid such as hydrogen chloride in an organic solvent such as dichloromethane.

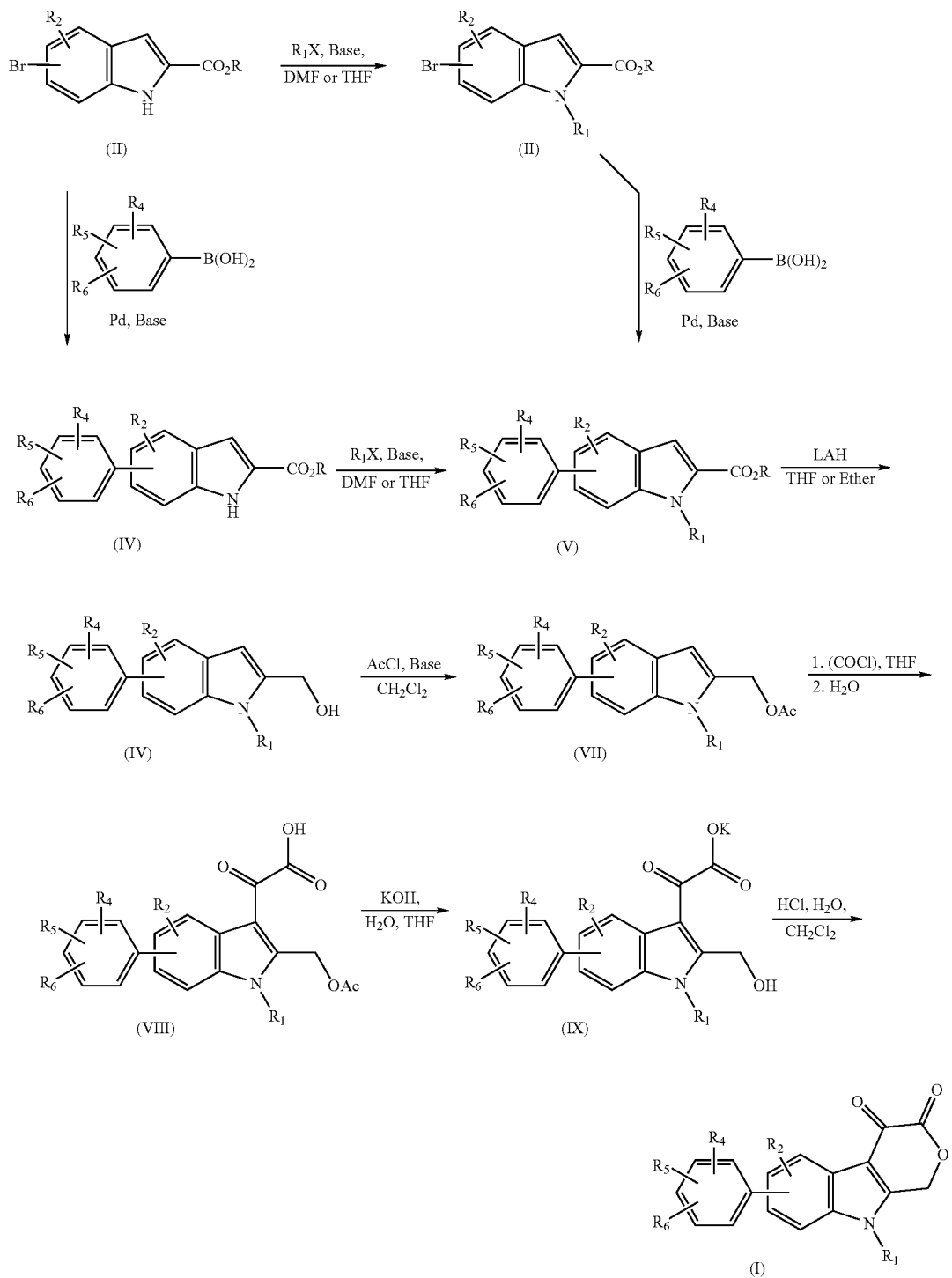

This invention also provides pharmaceutical compositions comprising a pharmaceutically or therapeutically effective amount of a compound of this invention, or a pharmaceutically acceptable salt or ester form thereof, either alone or in combination with one or more pharmaceutically acceptable carriers or excipients (i.e. pharmaceutically acceptable materials with no pharmacological effects). It will be understood that a pharmaceutically or therapeutically effective amount of a compound herein refers to an amount of the compound in question which will sufficiently inhibit the serine protease inhibitor PAI-1 in the mammal in need thereof to a sufficient extent to provide a desirable improvement in the condition in question or provide sufficient inhibition of the serine protease inhibitor PAI-1 to prevent, inhibit or limit the onset of the physiological basis for the malady or condition in question.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure, stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid, which is in admixture with the finely divided active ingredient. In tablets, the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions, which are sterile solutions or suspensions, can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physicians direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of PAI-1 and the patients symptomatic relief analysis may be used to determine whether a larger dose is indicated. Based upon the data presented below, the projected daily dose for both human and veterinary use will be from about 25 to about 200 milligrams/kilogram per day, and more usually, from about 50 to about 100 milligrams/kilogram per day.

The ability of the compounds of this invention to inhibit plasminogen activator inhibitor-1 was established by the following experimental procedures:

Primary Screen for the PAI-1 Inhibition

Test compounds were dissolved in DMSO at a final concentration of 10 mM, then diluted 100× in physiologic buffer. The inhibitory assay was initiated by the addition of the test compound (1–100 µM final concentration, maximum DMSO concentration of 0.2%) in a pH 6.6 buffer containing 140 nM recombinant human plasminogen activator inhibitor-1 (*Molecular Innovations*, Royal Oak, Mich.). Following a 1 hour incubation at room temperature, 70 nM of recombinant human tissue plasminogen activator (tPA) was added, and the combination of the test compound, PAI-1 and tPA was incubated for an additional 30 minutes. Following the second incubation, Spectrozyme-tPA (*American Diagnostica*, Greenwich, Conn.), a chromogenic substrate for tPA, was added and absorbance read at 405 nm at 0 and 60 minutes. Relative PAI-1 inhibition was equal to the residual tPA activity in the presence of the test compound and PAI-1. Control treatments included the complete inhibition of tPA by PAI-1 at the molar ratio employed (2:1), and the absence of any effect of the test compound on tPA alone.

Assay for Determining $IC_{50}$ of Inhibition of PAI-1

This assay is based upon the non-SDS dissociable interaction between tPA and active PAI-1. Assay plates were initially coated with human tPA (10 µg/ml). Test compounds were dissolved in DMSO at 10 mM, then diluted with physiologic buffer (pH 7.5) to a final concentration of 1–50 µM. Test compounds were incubated with human PAI-1 (50 ng/ml) for 15 minutes at room temperature. The tPA-coated plate was washed with a solution of 0.05% Tween 20 and 0.1% BSA, then the plate was blocked with a solution of 3% BSA. An aliquot of the test compound/PAI-1 solution was then added to the tPA-coated plate, incubated at room temperature for 1 hour, and washed. Active PAI-1 bound to the plate was assessed by adding an aliquot of a 1:1000 dilution of the 33B8 monoclonal antibody against human PAI-1, and incubating the plate at room temperature for 1 hour (*Molecular Innovations*, Royal Oak, Mich.). The plate was again washed, and a solution of goat anti-mouse IgG-alkaline phosphatase conjugate is added at a 1:50,000 dilution in goat serum. The plate was incubated 30 minutes at room temperature, washed, and a solution of alkaline phosphatase substrate is added. The plate was incubated 45 minutes at room temperature, and color development is determined at $OD_{405\ nm}$. The quantitation of active PAI-1 bound to tPA at varying concentrations of the test compound was used to determine the $IC_{50}$. Results were analyzed using a logarithmic best-fit equation. The assay sensitivity was 5 ng/ml of human PAI-1 as determined from a standard curve ranging from 0–100 ng/ml.

The compounds of the present invention inhibited Plasminogen Activator Inhibitor-1 as summarized in Table I.

TABLE I

| Example | $IC_{50}$ uM | % inhibition at 25 uM |
| --- | --- | --- |
| 1 | 2.3 | — |
| 2 | — | 34 |
| 3 | — | 22 |
| 4 | 29.5 | — |
| 5 | 26.6 | — |
| 6 | 34.8 | — |
| 7 | — | 6 |
| 8 | 4.83 | — |
| 9 | — | 40 |
| 10 | — | 59 |
| 11 | — | 30 |
| 12 | — | 40 |
| 13 | — | 36 |

EXAMPLE 1

9-(4-Methylbenzyl)-6-[4-(trifluoromethoxy)phenyl]-1,9-dihydropyrano[3,4-b]indole-3,4-dione Step 1

Ethyl 5-bromo-1-(4-methylbenzyl)-1H-indole-2-carboxylate

NaH (60%, 3.88 g, 96.98 mmol) was added portionwise to a stirring solution of ethyl 5-bromo-1H-indole-2-Carboxylate (20.0 g, 74.6 mmol) in DMF (140 mL) at 0° C. under a nitrogen atmosphere over a period of 10 min. The mixture was then warmed to room temperature. After the reaction mixture was stirred at room temperature for one hour, 4-methylbenzyl bromide (14.2 g, 74.6 mmol) was added and the mixture was stirred at room temperature overnight. The reaction was quenched with aqueous ammonium chloride and diluted with water. The aqueous mixture was extracted with ethyl acetate. The organic extract was washed with water and brine, dried over anhydrous magnesium sulfate. This mixture was concentrated to give a semi-solid contained 0.8 mole equivalent DMF. Mass spectrum (ESI, [M+H]$^+$) m/z 372. $^1$H NMR (400 MHz, DMSO-d$_6$) δ 7.93 (d, 1H, J=7.94 Hz), 7.55 (d, 1H, J=9.01 Hz), 7.40 (dd, 1H, J=8.85 and 1.98 Hz), 7.32 (s, 1H), 7.04 (d, 2H, J=7.96 Hz), 6.90 (d, 2H, J=7.94 Hz), 5.79 (s, 2H), 4.28 (q, 2H), 2.20 (s, 3H), and 1.28 ppm (t, 3H).

Step 2

Ethyl 1-(4-methylbenzyl)-5-[4-(trifluoromethoxy)phenyl]-1H-indole-2-carboxylate

A mixture of ethyl 5-bromo-1-(4-methylbenzyl)-1H-indole-2-Carboxylate (5.8 g, 15.54 mmol), 4-(trifluoromethoxy)phenylboronic acid (8.2 g, 38.85 mmol), potassium carbonate (5.4 g, 38.85 mmol), [1'1'-bis(diphenylphosphino)-ferrocene]dichloropalladium(II) complex with methylene (1:1) (4.41 g, 5.44 mmol) in dioxane-water (10:1, 154 mL) was stirred at 70° C. for two days. The reaction mixture was diluted with water and extracted with ethyl acetate. The organic extract was washed with water and brine, and then concentrated to an oil. This residue was crystallized from ethyl ether to afford the title compound as an off-white solid, m.p. 77–78° C. Mass spectrum (ESI, [M+H]$^+$) m/z 454. $^1$H NMR (400 MHz, DMSO-d$_6$) δ 8.00 (s, 1H), 7.78 (d, 2H, J=8.70 Hz), 7.67 (d, 1H, J=8.85 Hz), 7.61 (dd, 1H, J=8.70 and 1.68 Hz), 7.44 (s, 1H), 7.42–7.41 (m, 3H), 7.06 (d, 2H, J=7.94 Hz), 6.94 (d, 2H, J=8.09 Hz), 5.83 (s, 2H), 4.29 (q, 2H), 2.21 (s, 3H), and 1.30 ppm (t, 3H).

Elemental Analysis for $C_{26}H_{22}F_3NO_3$: Calculated: C, 68.87; H, 4.89; N, 3.09. Found: C, 69.00; H, 4.66; N, 3.06.

Step 3

{1-(4-Methylbenzyl)-5-[4-(trifluoromethoxy)phenyl]-1H-indol-2-yl}methanol

Lithium aluminum hydride (0.244 g, 6.1 mmol) was added portionwise to a stirring solution of ethyl 1-(4-methylbenzyl)-5-(trifluoromethoxy)phenyl]-1H-indole-2-Carboxylate (2.0 g, 4.4 mmol) in ethyl ether (17 mL) at 0° C. under a nitrogen atmosphere over a period of 5 minutes. The mixture was then warmed up to room temperature. After the reaction mixture was stirred at room temperature for 5 hours, the reaction was carefully quenched with water and filtered. The filtrate was extracted with ethyl acetate. The organic extract was washed with water and brine, dried over anhydrous magnesium sulfate and evaporated to afford the title compound as a white solid (1.56 g, 86%). Mass spectrum (ESI, [M+H]$^+$) m/z 412.

$^1$HNMR (400 MHz, DMSO-d$_6$): δ 7.81 (s, 1H), 7.76 (d, 2H, J=6.71 Hz), 7.45–7.35 (m, 4H), 7.08 (d, 2H, J=7.74 Hz), 6.96 (d, 2H, J=8.09 Hz), 6.50 (s, 1H), 5.44 (s, 2H), 5.35 (t, 1H), 4.60 (d, 2H), and 2.23 ppm (t, 3H). Elemental Analysis for $C_{24}H_{20}F_3NO_2$: Calculated: C, 70.07; H, 4.90; N, 3.40. Found: C, 69.80; H, 4.75; N, 3.34.

Step 4

{1-(4-Methylbenzyl)-5-[4-(trifluoromethoxy)phenyl]-1H-indol-2-yl}methyl acetate

Acetyl chloride (0.222 mL, 3.08 mmol) was added to a stirring solution of {1-(4-methylbenzyl)-5-[4-(trifluoromethoxy)phenyl]-1H-indol-2-yl}methanol (0.507 g, 1.23 mmol) and N,N-diisopropylethylamine (0.547 mL, 3.08 mmol) in methylene chloride (8 mL) at 0° C. under a nitrogen atmosphere over a period of 5 minutes. After the reaction mixture was stirred at room temperature overnight, the reaction was quenched carefully with water. The aqueous mixture was extracted with ethyl acetate. The organic extract was washed with water and brine, dried over anhydrous magnesium sulfate and evaporated to afford the title compound as a solid (0.557 g, 99.6%), mp: 125–126° C. Mass spectrum (ESI, [M+H]$^+$) m/z 454. $^1$HNMR (400 MHz, DMSO-d$_6$): δ 7.86 (s, 1H), 8.77 (d, 2H, J=8.96 Hz), 7.48–7.40 (m, 4H), 7.09 (d, 2H, J=7.94 Hz), 6.90 (d, 2H, J=7.94 Hz), 6.70 (s, 1H), 5.44 (s, 2H), 5.23 (s, 2H), 2.23 (s, 3H), and 1.85 ppm (s, 3H).

Elemental Analysis for $C_{26}H_{22}F_3NO_3$: Calculated: C, 68.32; H, 4.94; N, 3.07. Found: C, 67.96; H, 4.57; N, 2.96.

Step 5

{2-[(Acetyloxy)methyl]-1-(4-methylbenzyl)-5-[4-(trifluoromethoxy)phenyl]-1H-indol-3-yl}(oxo)acetic acid Oxalyl chloride (1.05 mL) was added dropwise to a stirring solution of {1-(4-methylbenzyl)-5-[4-(trifluoromethoxy)phenyl]-1H-indol-2-yl}methyl acetate (0.515 g) in THF (17 mL) at room temperature over a period of 5 minutes under a nitrogen atmosphere. After the reaction mixture was stirred at room temperature for 4 hours, the reaction was quenched carefully with water. The aqueous mixture was extracted with ethyl acetate. The extract was washed with water, and brine, dried over anhydrous magnesium sulfate, and concentrated to give the title compound as a light brown solid, mp: 79–80° C. Mass spectrum (ESI, [M–H]$^-$) m/z 524. $^1$HNMR (400 MHz, DMSO-d$_6$): δ 14.50 (br s, 1H), 8.20 (s, 1H), 7.74 (d, 2H, J=8.55 Hz), 7.70 (d, 1H, J=8.69 Hz), 7.62 (d, 1H, J=8.55 Hz), 7.47 (d, 2H, J=8.25 Hz), 7.15 (d, 2H, J=7.88 Hz), 6.99 (d, 2H, J=7.78 Hz), 5.64 (s, 2H), 5.53 (s, 2H), 2.25 (s, 3H), and 1.83 ppm (s, 3H).

Elemental Analysis for $C_{28}H_{22}F_3NO_6$: Calculated: C, 64.00; H, 2.67; N, 2.67. Found: C, 63.77; H, 3.99; N, 2.65.

Step 6

{2-(Hydroxymethyl)-1-(4-methylbenzyl)-5-[4-(trifluoromethoxy)phenyl]-1H-indol-3-yl}(oxo)acetic acid, potassium salt A solution of {2-[(acetyloxy)methyl]-1-(4-methylbenzyl)-5-[4-(trifluoromethoxy)phenyl]-1H-indol-3-yl}(oxo) acetic acid (0.50 g, 0.96 mmol) and aqueous potassium hydroxide (1.0 N, 2.38 mL, 2.38 mmol) in THF:water (1:1, 16 mL) was stirred at room temperature for 4 h. The reaction mixture was evaporated to dryness. The residual solid was stirred in water:hexane (8:92, 100 mL) and filtered to give the title compound as a white solid (0.4 g), mp: 248–249.5° C. Mass spectrum (ESI, [M–H]$^-$) m/z 482. $^1$HNMR (400 MHz, DMSO-d$_6$): δ 8.51 (s, 1H), 7.73 (d, 2H, J=8.86 Hz), 7.50 (d, 1H, J=8.56 Hz), 7.45 (d, 1H, J=8.55 Hz), 7.43 (d, 2H, J=7.94 Hz), 7.09 (d, 2H, J=8.09 Hz), 7.05 (d, 2H, J=8.09 Hz), 5.74 (t, 1H), 5.55 (s, 2H), 4.80 (d, 2H, J=6.80 Hz), and 2.23 ppm (s, 3H).

Elemental Analysis for $C_{26}H_{20}F_3NO_5 \cdot 1.0$ K.0.8 H$_2$O: Calculated: C, 58.27; H, 3.87; N, 2.61. Found: C, 58.14; H, 3.82; N, 2.59.

Step 7

9-(4-Methylbenzyl)-6-[4-(trifluoromethoxy)phenyl]-1,9-dihydropyrano[3,4-b]indole-3,4-dione {2-(Hydroxymethyl)-1-(4-methylbenzyl)-5-[4-(trifluoromethoxy)phenyl]-1H-indol-3-yl}(oxo) acetic acid, potassium salt (0.355 g) was partitioned between methylene chloride (400 mL) and 15% aqueous HCl (100 mL) with stirring. The organic layer was separated, washed with water and evaporated to afford the title compound as an off-white solid (0.304 g), mp: 243–244° C. Mass spectrum (ESI, [M–H]$^-$) m/z 464.

$^1$HNMR (400 MHz, DMSO-d$_6$): δ 8.23 (s, 1H), 7.81 (d, 2H, J=7.49 Hz), 7.77 (d, 1H, J=8.40 Hz), 7.67 (d, 1H, J=8.71 Hz), 7.46 (d, 2H, J=7.94 Hz), 7.16 (s, 4H,) 5.92 (s, 2H), 5.50 (s, 2H), and 2.25 ppm (s, 3H). Elemental Analysis for $C_{26}H_{18}F_3NO_4$: Calculated: C, 67.10; H, 3.90; N, 3.01. Found: C, 66.82; H, 3.71; N, 2.91.

EXAMPLE 2

9-Benzyl-6-[4-(trifluoromethoxy)phenyl]-1,9-dihydropyrano[3,4-b]indole-3,4-dione Step 1

Ethyl 5-bromo-1-benzyl-1H-indole-2-carboxylate

The title compound was prepared from ethyl 5-bromo-1H-indole-2-Carboxylate and benzyl bromide in substantially the same manner, as described in step 1 of Example 1. The product was obtained as a light yellow solid. Mass spectrum (ESI, [M+H]$^+$) m/z 358. $^1$H NMR (300 MHz, DMSO-d$_6$) δ 7.94 (s, 1H), 7.55 (d, 1H, J=9.01 Hz), 7.42 (d, 1H, J=8.85 Hz), 7.34 (s, 1H), 7.30–7.21 (m, 3H), 6.99 (d, 2H, J=7.94 Hz), 5.85 (s, 2H), 4.28 (q, 2H), and 1.28 ppm (t, 3H).

Elemental Analysis for $C_{18}H_{16}BrNO_2$: Calculated: C, 60.35; H, 4.50; N, 3.91. Found: C, 69.19; H, 4.51; N, 3.75.

Step 2

Ethyl 1-benzyl-5-[4-(trifluoromethoxy)phenyl]-1H-indole-2-carboxylate

The title compound was prepared from ethyl 5-bromo-1-benzyl-1H-indole-2-Carboxylate and 4-(trifluoromethoxy) phenylboronic acid in substantially the same manner, as described in step 2 of Example 1. The product was obtained as an oil.

Mass spectrum (ESI, [M+H]$^+$) m/z 440. $^1$H NMR (400 MHz, DMSO-d$_6$) δ 8.01 (s, 1H), 7.79 (d, 2H, J=8.86 Hz), 7.67 (d, 1H, J=8.85 Hz), 7.62 (dd, 1H, J=8.70 and 1.68 Hz), 7.44–7.42 (m, 2H), 7.28–7.20 (m, 3H), 7.04 (d, 2H, J=7.94 Hz), 5.88 (s, 2H), 4.28 (q, 2H), 1.29 (t, 3H).

Step 3

{1-benzyl-5-[4-(trifluoromethoxy)phenyl]-1H-indol-2-yl}methanol

The title compound was prepared from ethyl 1-benzyl-5-[4-(trifluoromethoxy)phenyl]-1H-indole-2-Carboxylate (step 3 of Example 1) and lithium aluminum in substantially the same manner, as described in step 1 of Example 21. The product was obtained as a white solid, mp: 108–109° C. Mass spectrum (ESI, [M+H]$^+$) m/z 398. $^1$H NMR (400 MHz, DMSO-d$_6$) δ 7.82 (s, 1H), 7.76 (d, 2H, J=8.86 Hz), 7.42–7.36 (m, 4H) 7.29 (d, 1H, J=7.03 Hz), 7.27 (d, 1H, J=7.63 Hz), 7.23–7.20 (m, 1H), 7.06 (d, 2H, J=7.03 Hz), 6.52 (s, 1H), 5.50 (s, 2H), 5.36 (t, 1H), and 4.60 ppm (d, 2H).

Elemental Analysis for $C_{23}H_{18}F_3NO_2$: Calculated: C, 69.52; H, 4.57; N, 3.52. Found: C, 69.21; H, 4.38; N, 3.40.

Step 4

{1-benzyl-5-[4-(trifluoromethoxy)phenyl]-1H-indol-2-yl}methyl acetate

The title compound was prepared from {1-benzyl-5-[4-(trifluoromethoxy)phenyl]-1H-indol-2-yl}methanol and acetyl chloride in substantially the same manner, as described in step 4 of Example 1. The product was obtained as an oil. Mass spectrum (ESI, [M+H]$^+$) m/z 440. $^1$H NMR (300 MHz, DMSO-d$_6$) δ 7.88 (s, 1H), 7.77 (d, 2H, J=8.87 Hz), 7.48–7.40 (m, 4H), 7.29–7.22 (m, 3H), 7.00 (d, 2H, J=7.01 Hz), 6.72 (s, 1H), 5.50 (s, 2H), 5.24 (s, 2H), and 1.80 ppm (s, 3H).

Elemental Analysis for C$_{25}$H$_{20}$F$_3$NO$_3$: Calculated: C, 68.33; H, 4.59; N, 3.19. Found: C, 68.19; H, 4.70; N, 3.06.

Step 5

{2-[(Acetyloxy)methyl]-1-benzyl-5-[4-(trifluoromethoxy)phenyl]-1H-indol-3-yl}(oxo)acetic acid The title compound was prepared from {1-benzyl-5-[4-(trifluoromethoxy)phenyl]-1H-indol-2-yl}methyl acetate and oxalyl chloride in substantially the same manner, as described in step 5 of Example 1. The product was obtained as a brown solid; mp: 85–86° C. Mass spectrum (ESI, [M–H]$^-$) m/z 510. $^1$H NMR (400 MHz, DMSO-d$_6$) δ 14.40 (br s, 1H), 8.20 (s, 1H), 7.76 (d, 2H, J=6.72 Hz), 7.72 (d, 1H, J=8.70 Hz), 7.63 (d, 1H, J=8.70 Hz), 7.48 (d, 2H, J=8.24 Hz), 7.34–7.25(m, 3H), 7.08(d, 1H, J=7.23 Hz), 5.70 (s, 2H), 5.53 (s, 2H), and 1.78 ppm (s, 3 H).

Elemental Analysis for C$_{27}$H$_{20}$F$_3$NO$_6$: Calculated: C, 63.41; H, 3.94; N, 2.74. Found: C, 63.02; H, 3.97; N, 2.64.

Step 6

{2-(Hydroxymethyl)-1-benzyl-5-[4-(trifluoromethoxy)phenyl]-1H-indol-3-yl}(oxo)acetic acid, potassium salt The title compound was prepared from {2-[(acetyloxy)methyl]-1-benzyl-5-[4-(trifluoromethoxy)phenyl]-1H-indol-3-yl}(oxo)acetic acid and aqueous potassium hydroxide in substantially the same manner, as described in step 6 of Example 1. The product was obtained as a white solid; mp: 280–282° C. Mass spectrum (ESI, [M–H]$^-$) m/z 468. $^1$H NMR (400 MHz, DMSO-d$_6$) δ 8.51 (s, 1H), 7.72 (d, 2H, J=8.70 Hz), 7.52 (d, 1H, J=8.55 Hz), 7.47–7.43 (m, 3H), 7.31–28 (m, 2H), 7.23 (d, 1H, J=7.18 Hz), 7.15 (d, 2H, J=7.18 Hz), 5.75 (t, 1H), 5.62 (s, 2H), and 4.81 ppm (d, 2H, J=6.72 Hz).

Elemental Analysis for C$_{25}$H$_{18}$F$_3$NO$_5$.1.0 K.1.0 H$_2$O: Calculated: C, 57.14; H, 3.64; N, 2.67. Found: C, 57.05; H, 3.42; N, 2.55.

Step 7

9-Benzyl-6-[4-(trifluoromethoxy)phenyl]-1,9-dihydropyrano[3,4-b]indole-3,4-dione The title compound was prepared from {2-(Hydroxymethyl)-1-benzyl-5-[4-(trifluoromethoxy)phenyl]-1H-indol-3-yl}(oxo)acetic acid, potassium salt and aqueous HCl in substantially the same manner, as described in step 7 of Example 1. The product was obtained as an off-white solid; mp: 239–240° C. Mass spectrum (ESI, [M+H]$^+$) m/z 452. $^1$H NMR (400 MHz, DMSO-d$_6$) δ 8.24 (s, 1H), 7.81 (dd, 2H, J=8.86 and 2.14 Hz), 7.74 (d, 1H, J=8.56 Hz), 7.68 (dd, 1H, J=8.54 and 1.83 Hz), 7.46 (d, 2H, J=7.94 Hz), 7.37–7.26 (m, 5H,), 5.93 (s, 2H), and 5.56 ppm (s, 2H).

Elemental Analysis for C$_{25}$H$_{16}$F$_3$NO$_4$: Calculated: C, 66.52; H, 3.57; N, 3.10. Found: C, 66.59; H, 3.50; N, 3.04.

EXAMPLE 3

9-(4-Methylbenzyl)-6-(3-methylphenyl)-1,9-dihydropyrano[3,4-b]indole-3,4-dione

Step 1

Ethyl 1-(4-methylbenzyl)-5-(3-methylphenyl)-1H-indole-2-carboxylate

The title compound was prepared from ethyl 5-bromo-1-(4-methylbenzyl)-1H-indole-2-Carboxylate (step 1 of Example 1) and 3-methylphenylboronic acid in substantially the same manner, as described in step 2 of Example 1. The product was obtained as a solid. Mass spectrum (ESI, [M+H]$^+$) m/z 384. $^1$H NMR (400 MHz, DMSO-d$_6$) δ 7.95 (s, 1H), 7.63 (d, 1H, J=7.70 Hz), 7.60 (d, 1H, J=8.47 Hz), 7.48 (s, 1H), 7.44 (d, 1H, J=7.95 Hz), 7.39 (s, 1H), 7.33 (t, 1H, J=7.63 Hz), 7.14 (d, 1H, J=7.49 Hz), 7.07 (d, 2H, J=7.94 Hz), 6.93 (d, 2H, J=7.94 Hz), 5.82 (s, 2H), 4.29 (q, 2H, J=7.17 Hz), 2.37 (s, 3H), 2.21 (s, 3H), and 1.30 ppm (t, 3H, J=7.18 Hz).

Step 2

[1-(4-Methylbenzyl)-5-(3-methylphenyl)-1H-indol-2-yl]methanol

The title compound was prepared from ethyl 1-(4-methylbenzyl)-5-(3-methylphenyl)-1H-indole-2-Carboxylate and lithium aluminum in substantially the same manner, as described in step 3 of Example 1. The product was obtained as a white solid. Mass spectrum (ESI, [M+H]$^+$) m/z 342. $^1$H NMR (400 MHz, DMSO-d$_6$)δ 7.77 (s, 1H), 7.46 (s, 1H), 7.42 (d, 1H, J=7.79 Hz), 7.37 (d, 1H, J=8.55 Hz), 7.33 (d, 1H, J=8.56 Hz), 7.31 (d, 1H, J=7.02 Hz), 7.29 (d, 1H, J=7.48 Hz), 7.10–7.07 (m, 4H), 6.96 (d, 2H, J=7.94 Hz), 6.48 (s, 1H), 5.54 (s, 2H), 5.33 (s, 1H), 4.60 (s, 2H), 2.36 (s, 3H), and 2.23 ppm (s, 3H).

Elemental Analysis for C$_{24}$H$_{23}$NO.0.5 H$_2$O: Calculated: C, 82.25; H, 6.90; N, 4.00. Found: C, 82.05; H, 6.98; N, 3.88.

Step 3

[1-(4-Methylbenzyl)-5-(3-methylphenyl)-1H-indol-2-yl]methyl acetate

The title compound was prepared from [1-(4-methylbenzyl)-5-(3-methylphenyl)-1H-indol-2-yl]methanol and acetyl chloride in substantially the same manner, as described in step 4 of Example 1. The product was obtained as a brown oil. Mass spectrum (ESI, [M+H]$^+$) m/z 384. $^1$H NMR (400 MHz, DMSO-d$_6$) δ 7.82 (s, 1H), 7.47 (s, 1H), 7.45–7.40 (m, 3H), 7.31 (t, 1H, J=7.74 Hz), 7.13–7.08 (m, 3H), 6.90 (d, 2H, J=8.09 Hz), 6.68 (s, 1H), 5.43 (s, 2H), 5.22 (s, 2H), 2.36 (s, 3H), 2.23 (s, 3H), and 1.85 ppm (s, 3H).

Elemental Analysis for C$_{26}$H$_{25}$NO$_2$: Calculated: C, 81.43; H, 6.57; N, 3.65. Found: C, 81.75; H, 6.67; N, 3.26.

Step 4

[2-[(Acetyloxy)methyl]-1-(4-methylbenzyl)-5-(3-methylphenyl)-1H-indol-3-yl](oxo)acetic acid The title compound was prepared from [1-(4-methylbenzyl)-5-(3-methylphenyl)-1H-indol-2-yl]methyl acetate and oxalyl chloride in substantially the same manner, as described in step 5 of Example 1. The product was obtained as a brown solid; mp: 89–90° C. Mass spectrum (ESI, [M–H]$^-$) m/z 454. $^1$H NMR (400 MHz, DMSO-d$_6$) δ 8.18 (s, 1H), 7.67 (d, 1H, J=8.69 Hz), 7.59 (dd, 1H, J=7.17 and 1.53 Hz), 7.44–7.41 (m, 2H),), 7.36 (t, 1H, J=7.48 Hz), 7.18 (d, 1H, J=7.23 Hz), 7.13 (d, 1H, J=7.94 Hz), 5.63 (s, 2H), 5.53 (s, 2H), 2.39 (s, 3H), 2.24 (s, 3H), and 1.83 ppm (s, 3H).

Elemental Analysis for $C_{28}H_{25}NO_5$.0.5 $H_2O$: Calculated: C, 72.40; H, 5.64; N, 3.02. Found: C, 72.41; H, 5.44; N, 2.96.

Step 5

9-(4-Methylbenzyl)-6-(3-methylphenyl)-1,9-dihydropyrano[3,4-b]indole-3,4-dione

The title compound was prepared from [2-[(acetyloxy)methyl]-1-(4-methylbenzyl)-5-(3-methylphenyl)-1H-indol-3-yl](oxo)acetic acid and aqueous potassium hydroxide in substantially the same manner, as described in step 6 of Example 1 followed by the treatment with aqueous HCl in substantially the same manner, as described in step 7 of Example 1. The product was obtained as a white solid; mp: 216–217° C. Mass spectrum (ESI, [M+H]$^+$) m/z 396. $^1$H NMR (400 MHz, DMSO-d$_6$) δ 8.21 (s, 1H), 7.71 (d, 1H, J=8.56 Hz), 7.64 (dd, 1H, J=8.75 and 1.28 Hz), 7.49 (s, 1H), 7.46 (d, 1H, J=8.09 Hz), 7.36 (t, 1H, J=7.63 Hz), 7.19–7.14 (m, 5H,), 5.91 (s, 2H), and 5.49 (s, 2H), 2.39 (s, 3H), 2.26 ppm (s, 3H), Elemental Analysis for $C_{26}H_{21}NO_3$.0.4 $H_2O$: Calculated: C, 77.56; H, 5.46; N, 3.48. Found: C, 77.41; H, 5.46; N, 3.49.

EXAMPLE 4

9-(4-tert-butylbenzyl)-6-(3-methylphenyl)-1,9-dihydropyrano[3,4-b]indole-3,4-dione Step 1

(5-Bromo-1H-indol-2-yl)methanol

The title compound was prepared from ethyl 5-bromo-1H-indole-2-Carboxylate and lithium aluminum in substantially the same manner, as described in step 3 of Example 1. The product was obtained as a solid; mp: 111–112° C. Mass spectrum (ESI, [M–H]$^-$) m/z 224. $^1$H NMR (400 MHz, DMSO-d$_6$) δ 7.62 (s, 1H), 7.27 (d, 1H, J=8.02 Hz), 7.12 (d, 1H, J=8.02 Hz), 6.25 (s, 1H), 5.29 (t, 1H, J=5.50 Hz), 4.59 ppm (d, 2H, J=5.65 Hz).

Elemental Analysis for $C_9H_8BrNO$: Calculated: C, 47.82; H, 3.57; N, 6.20. Found: C, 47.94; H, 3.42; N, 6.20.

Step 2

[5-(3-Methylphenyl)-1H-indol-2-yl]methyl acetate

A mixture of (5-bromo-1H-indol-2-yl)methanol (9 g, 39.8 mmol), 3-methylbenzeneboronic acid (6.14 g, 43.78 mmol), potassium carbonate (13.75 g, 99.5 mmol), palladium(II) acetate (0.045 g) and tetrabutylammonium bromide (12.84 g, 39.8 mmol) in 10% dioxane in water (degassed, 0.38 L) was stirred at 70° C. The reaction was monitored by TLC. Additional 3-methylbenzeneboronic acid (5.6 g, 39.8 mmol) was added. After no 5-bromo-1-(4-tert-butylbenzyl)-1H-indole was detected by TLC, the reaction was cooled to room temperature and the solvent was decanted. The residual thick oil was stirred with hexane. The hexane was decanted and the residue was partitioned between water and ethyl acetate. The ethyl acetate layer was separated, washed with water filtered and concentrated. The residue was purified by flash column chromatography using hexane/ethyl acetate (55:45) as an eluant to give [5-(3-Methylphenyl)-1H-indol-2-yl]methanol as a brown solid (6.0 g). Reaction of [5-(3-Methylphenyl)-1H-indol-2-yl]methanol with acetyl chloride according to the procedure described in step 4 of Example 1 afforded the title compound as an oil (3.94 g); Mass spectrum (ESI, [M–H]$^-$) m/z 278. $^1$H NMR (400 MHz, DMSO-d$_6$) δ 7.76 (s, 1H), 7.46 (s, 1H), 7.42–7.36 (m, 3H), 7.30 (s, 1H), 7.10 (d, 1H, J=7.48 Hz), 6.50 (s, 1H), 2.37 (s, 3H), and 2.07 ppm (s, 3H).

Step 3

[1-(4-tert-Butylbenzyl)-5-(3-methylphenyl)-1H-indol-2-yl]methyl acetate

Potassium carbonate (0.3 g, 2.15 mmol) was added to a stirring solution of 5-(3-methylphenyl)-1H-indol-2-yl]methyl acetate (0.5 g, 1.79 mmol) in DMF (5 mL) at room temperature under a nitrogen atmosphere. 4-tert-Butylbenzyl bromide (0.356 g, 1.88 mmol) was added and the mixture was stirred at room temperature overnight. The reaction was monitored by TLC. An additional amount of 4-tert-butylbenzyl bromide (0.34 g, 1.8 mmol) was added and stirring continued at room temperature for three days. The reaction was quenched with aqueous ammonium chloride, diluted with water and extracted with ethyl acetate. The organic extract was washed with water and brine, dried over anhydrous magnesium sulfate and evaporated to dryness. The residue was purified by flash column chromatography using hexane/ethyl acetate (85:15) as an eluant to give the title compound as a light brown oil (0.284 g). Mass spectrum (ESI, [M+H]$^+$) m/z 426. $^1$H NMR (400 MHz, DMSO-d$_6$) δ 7.83 (s, 1H), 7.49–7.47 (m, 2H), 7.44–7.41 (m, 2H), 7.32–7.29 (m, 3H), 7.11 (d, 1H, J=7.49 Hz), 6.91 (d, 2H, J=8.24 Hz), 6.69 (s, 1H), 5.44 (s, 2H), 5.23 (s, 2H), 2.36 (s, 3H), 1.78 (s, 3H), and 1.21 ppm (s, 9H).

Elemental Analysis for $C_{29}H_{31}NO_2$.0.3 $H_2O$: Found: C, 80.82; H, 7.39; N, 3.25. Calculated: C, 80.90; H, 7.45; N, 3.17.

Step 4

[2-[(Acetyloxy)methyl]-1-(4-tert-butylbenzyl)-5-(3-methylphenyl)-1H-indol-3-yl](oxo)acetic acid The title compound was prepared from [1-(4-tert-butylbenzyl)-5-(3-methylphenyl)-1H-indol-2-yl]methyl acetate and oxalyl chloride in substantially the same manner, as described in step 5 of Example 1. The product was obtained as a light brown solid; mp: 91–92° C. Mass spectrum (ESI, [M–H]$^-$) m/z 496. $^1$H NMR (400 MHz, DMSO-d$_6$) δ 8.18 (s, 1H), 7.72 (d, 2H, J=8.71 Hz), 7.61 (dd, 1H, J=8.70 and 1.38 Hz), 7.45–7.41 (m, 2H), 7.38–7.33 (m, 3H), 7.18 (d, 1H, J=8.70 Hz), 7.00 (d, 2H, J=8.24 Hz), 5.64 (s, 2H), 5.53 (s, 2H), 2.39 (s, 3H), 1.76 (s, 3H), and 1.22 ppm (s, 9H).

Elemental Analysis for $C_{31}H_{31}NO_5 \cdot 0.5\ H_2O$: Calculated: C, 73.50; H, 6.37; N, 2.77. Found: C, 73.43; H, 6.57; N, 2.64.

Step 5

9-(4-tert-Butylbenzyl)-6-(3-methylphenyl)-1,9-dihydropyrano[3,4-b]indole-3,4-dione A solution of [2-[(acetyloxy)methyl]-1-(4-tert-butylbenzyl)-5-(3-methylphenyl)-1H-indol-3-yl](oxo)acetic acid (0.27 g, 0.63 mmol) and aqueous potassium hydroxide (1.0 N, 1.1 mL, 1.1 mmol) in THF:MeOH (1:1, 6.6 mL) was stirred at room temperature for 4 h. The reaction mixture was evaporated to dryness. The residue was washed with water and hexane to give an oil. This oil was partitioned between methylene chloride (80 mL) and 15% aqueous HCl (15 mL) with stirring. The organic layer was separated, washed with water and evaporated to afford the title compound as an off-white solid, mp: 196–197° C. Mass spectrum (ESI, [M+H]$^+$) m/z 438. $^1$HNMR (400 MHz, DMSO-d$_6$): δ 8.21 (s, 1H), 7.75 (d, 2H, J=8.55 Hz), 7.66 (dd, 1H, J=8.70 and 1.52 Hz), 7.50 (s, 1H), 7.47 (d, 1H, J=8.71 Hz), 7.38–7.35 (m, 3H), 7.20–7.17 (m, 3H), 5.92 (s, 2H), 5.50 (s, 2H), and 2.39 ppm (s, 3H).

Elemental Analysis for $C_{29}H_{27}NO_3 \cdot 0.5\ H_2O$: Calculated: C, 78.64; H, 6.28; N, 3.16. Found: C, 78.54; H, 6.46; N, 3.04

EXAMPLE 5

6-(Benzyloxy)-9-(4-methylbenzyl)-1,9-dihydropyrano[3,4-b]indole-3,4-dione

Step 1

[5-(Benzyloxy)-1H-indol-2-yl]methanol

The title compound was prepared from ethyl 5-(benzyloxy)-1H-indole-2-carboxylate and lithium aluminum hydride according to the procedure described in step 3 of Example 1. The product was obtained as a white solid, mp: 106–107° C. Mass spectrum (ESI, [M+H]$^+$) m/z 254. $^1$H NMR (400 MHz, DMSO-d$_6$) δ 10.80 (s, 1H), 7.45 (d, 2H, J=7.33 Hz), 7.37 (t, 2H, J=7.49 Hz), 7.30 (d, 1H, J=7.18 Hz), 7.20 (d, 1H, J=8.71 Hz), 7.04 (s, 1H), 6.74 (dd, 1H, J=8.70 and 1.46 Hz), 6.16 (s, 1H), 5.16 (t, 1H, J=5.49 Hz), 5.01 (s, 2H), 4.55 ppm (d, 2H, J=5.50 Hz).

Elemental Analysis for $C_{16}H_{15}NO_2$: Calculated: C, 75.87; H, 5.97; N, 5.53. Found: C, 75.96; H, 6.11; N, 5.41.

Step 2

[5-(Benzyloxy)-1H-indol-2-yl]methyl acetate

The title compound was prepared from [5-(benzyloxy)-1H-indol-2-yl]methanol and acetyl chloride in substantially the same manner, as described in step 4 of Example 1. The product was obtained as a gray solid. Mass spectrum (ESI, [M+H]$^+$) m/z 296. $^1$H NMR (400 MHz, DMSO-d$_6$) δ 11.03 (s, 1H), 7.45 (d, 2H, J=7.33 Hz), 7.38 (t, 2H, J=7.49 Hz), 7.30 (d, 1H, J=7.20 Hz), 7.24 (d, 1H, J=8.71 Hz), 7.08 (s, 1H), 6.81 (dd, 1H, J=8.70 and 1.45 Hz), 6.34 (s, 1H), 5.13 (s, 2H), 5.06 (s, 2H), 2.04 ppm (s, 3H).

Elemental Analysis for $C_{18}H_{17}NO_3 \cdot 0.2\ H_2O$: Calculated: C, 72.32; H, 5.87; N, 4.69. Found: C, 72.21; H, 5.75; N, 4.66.

Step 3

[5-(Benzyloxy)-1-(4-methylbenzyl)-1H-indol-2-yl] methyl acetate

The title compound was prepared from [5-(benzyloxy)-1H-indol-2-yl]methyl acetate and 4-methylbenzyl bromide in substantially the same manner, as described in step 3 of Example 4. The product was obtained as a white solid. Mass spectrum (ESI, [M+H]$^+$) m/z 400. $^1$H NMR (300 MHz, DMSO-d$_6$) δ 7.45 (d, 2H, J=8.34 Hz), 7.37 (t, 2H, J=7.19 Hz), 7.31 (d, 1H, J=7.30 Hz), 7.26 (d, 1H, J=7.56 Hz), 7.15 (d, 1H, J=2.44 Hz), 7.07 (d, 2H, J=8.76 Hz), 6.85 (d, 2H, J=8.81 Hz), 6.84 (s, 1H), 6.25 (s, 1H), 5.35 (s, 2H), 5.17 (s, 2H), 5.09 (s, 2H), 2.22 (s, 3H), 1.84 ppm (s, 3H).

Elemental Analysis for $C_{26}H_{25}NO_3$: Calculated: C, 78.17; H, 6.31; N, 3.51. Found: C, 78.01; H, 6.35; N, 3.46.

Step 4

[2-[(Acetyloxy)methyl]-5-(benzyloxy)-1-(4-methylbenzyl)-1H-indol-3-yl](oxo)acetic The title compound was prepared from [5-(benzyloxy)-1-(4-methylbenzyl)-1H-indol-2-yl]methyl acetate and oxalyl chloride in substantially the same manner, as described in step 5 of Example 1. The product was obtained as an off-white solid; mp: 91–92° C. Mass spectrum (ESI, [M−H]$^−$) m/z 470. $^1$H NMR (400 MHz, DMSO-d$_6$) δ 7.61 (s, 1H), 7.50 (s, 1H), 7.47 (d, 2H, J=8.24 Hz), 7.39 (t, 2H, J=7.64 Hz), 7.32 (d, 1H, J=7.02 Hz), 7.11 (d, 2H, J=8.10 Hz),), 7.03 (d, 1H, J=8.99 Hz), 6.95 (d, 2H, J=7.79 Hz), 5.54 (s, 2H), 5.46 (s, 2H), 5.10 (s, 2H), 2.23 (s, 3H), 1.82 ppm (s, 3H).

Elemental Analysis for $C_{28}H_{25}NO_6 \cdot 0.6\ H_2O$: Calculated: C, 69.73; H, 5.48; N, 2.90. Found: C, 69.60; H, 5.30; N, 2.80.

Step 5

6-(Benzyloxy)-9-(4-methylbenzyl)-1,9-dihydropyrano[3,4-b]indole-3,4-dione

The title compound was prepared from [2-[(acetyloxy)methyl]-5-(benzyloxy)-1-(4-methylbenzyl)-1H-indol-3-yl](oxo)acetic acid and aqueous potassium hydroxide according to the procedure described in step 6 of Example 1, followed by the treatment with aqueous HCl in substantially the same manner, as described in step 7 of Example 1. The product was obtained as an off-white solid; mp: 206–207° C.

Mass spectrum (ESI, [M+H]$^+$) m/z 412. $^1$H NMR (400 MHz, DMSO-d$_6$) δ 7.58 (s, 1H), 7.54 (d, 1H, J=9.01 Hz), 7.47 (d, 2H, J=7.33 Hz), 7.38 (t, 2H, J=8.63 Hz), 7.31 (t, 1H, J=7.18 Hz), 7.15–7.11 (m, 4H,), 7.05 (dd, 2H, J=9.44 and 2.44 Hz), 5.86 (s, 2H), 5.41 (s, 2H), 5.16 (s, 2H), 2.25 ppm (s, 3H). Elemental Analysis for $C_{26}H_{21}NO_4 \cdot 0.8\ H_2O$: Calculated: C, 73.33; H, 5.35; N, 3.29. Found: C, 73.16; H, 4.95; N, 3.20.

EXAMPLE 6

6-(Benzyloxy)-1,9-dihydropyrano[3,4-b]indole-3,4-dione

Step 1

[2-[(Acetyloxy)methyl]-5-(benzyloxy)-1H-indol-3-yl](oxo)acetic acid

The title compound was prepared from [5-(benzyloxy)-1H-indol-2-yl]methyl acetate (step 2 of Example 5) and oxalyl chloride following the procedure described in step 5 of Example 1. The product was obtained as a brown solid; mp: >165° C. (dec.).

Mass spectrum (ESI, [M−H]⁻) m/z 366. $^1$H NMR (400 MHz, DMSO-$d_6$) δ 12.42 (s, 1H), 7.51 (s, 1H), 7.48 (d, 2H, J=7.33 Hz), 7.43 (d, 1H, J=8.85 Hz), 7.39 (t, 2H, J=7.33 Hz), 7.32 (d, 1H, J=7.17 Hz), 6.99 (d, 1H, J=7.86 Hz), 5.41 (s, 2H), 5.10 (s, 2H), 2.13 ppm (d, 3H). Elemental Analysis for $C_{20}H_{17}NO_6$: Calculated: C, 65.39; H, 4.66; N, 3.81. Found: C, 65.37; H, 4.68; N, 3.83.

Step 2

6-(Benzyloxy)-1,9-dihydropyrano[3,4-b]indole-3,4-dione

The title compound was prepared from [2-[(acetyloxy)methyl]-5-(benzyloxy)-1H-indol-3-yl](oxo)acetic acid and aqueous potassium hydroxide in substantially the same manner, as described in step 6 of Example 1, followed by the treatment with aqueous HCl, as described in step 7 of Example 1. The product was obtained as a yellow solid; mp: >291° C. (dec.). Mass spectrum (ESI, [M−H]⁻) m/z 306. $^1$H NMR (400 MHz, DMSO-$d_6$) δ 12.37 (s, 1H), 7.54 (s, 1H), 7.49 (s, 1H), 7.48 (d, 2H, J=8.86 Hz), 7.39 (t, 2H, J=7.64 Hz), 7.32 (d, 1H, J=7.18 Hz), 7.04 (dd, 1H, J=8.71 and 2.59 Hz), 5.82 (s, 2H), and 5.16 ppm (s, 2H).

Elemental Analysis for $C_{18}H_{13}NO_4$: Calculated: C, 70.35; H, 4.26; N, 4.56. Found: C, 70.07; H, 4.17; N, 4.49.

EXAMPLE 7

6-(Benzyloxy)-9-(4-tert-butylbenzyl)-1,9-dihydropyrano[3,4-b]indole-3,4-dione

Step 1

[5-(Benzyloxy)-1-(4-tert-butylbenzyl)-1H-indol-2-yl]methyl acetate

The title compound was prepared from [5-(benzyloxy)-1H-indol-2-yl]methyl acetate and 4-tert-butylbenzyl bromide in substantially the same manner, as described in step 3 of Example 4. The product was obtained as a white solid; mp: 132–133° C.

Mass spectrum (ESI, [M+H]⁺) m/z 442. $^1$H NMR (400 MHz, DMSO-$d_6$) δ 7.45 (d, 2H, J=7.33 Hz), 7.38 (t, 2H, J=7.33 Hz), 7.32–7.27 (m, 4H), 7.16 (d, 1H, J=2.30 Hz), 6.88–6.84 (m, 3H), 6.53 (s, 1H), 5.36 (s, 2H), 5.18 (s, 2H), 5.08 (s, 2H), 1.77 (s, 3H), and 1.21 ppm (s, 9H). Elemental Analysis for $C_{29}H_{31}NO_3$: Calculated: C, 78.88; H, 7.08; N, 3.17. Found: C, 78.79; H, 7.07; N, 3.04.

Step 2

[2-[(Acetyloxy)methyl]-5-(benzyloxy)-1-(4-tert-butylbenzyl)-1H-indol-3-yl](oxo)acetic acid The title compound was prepared from [5-(Benzyloxy)-1-(4-tert-butylbenzyl)-1H-indol-2-yl]methyl acetate and oxalyl chloride in substantially the same manner, as described in step 5 of Example 1. The product was obtained as an off-white solid;

mp: 145–146° C. Mass spectrum (ESI, [M−H]⁻) m/z 512. $^1$H NMR (400 MHz, DMSO-$d_6$) δ 7.61 (d, 1H, J=2.14 Hz), 7.56 (d, 1H, J=9.16 Hz), 7.48 (d, 2H, J=7.18 Hz), 7.39 (t, 2H, J=7.33 Hz), 7.33–7.31 (m, 4H) 7.05 (dd, 1H, J=9.01 and 2.45 Hz), 6.96 (d, 1H, J=8.25 Hz), 5.56 (s, 2H), 5.46 (s, 2H), 5.11 (s, 2H), 1.75 (s, 3H), and 1.21 ppm (s, 9H). Elemental Analysis for $C_{31}H_{31}NO_6 \cdot 0.7 H_2O$: Calculated: C, 70.76; H, 6.21; N, 2.66. Found: C, 70.76; H, 6.39; N, 2.64.

Step 3

6-(Benzyloxy)-9-(4-tert-butylbenzyl)-1,9-dihydropyrano[3,4-b]indole-3,4-dione

The title compound was prepared from [2-[(acetyloxy)methyl]-5-(benzyloxy)-1-(4-tert-butylbenzyl)-1H-indol-3-yl](oxo)acetic acid and aqueous potassium hydroxide in substantially the same manner, as described in step 6 of Example 1, followed by the treatment with aqueous HCl, as described in step 7 of Example 1. The product was obtained as an off-white solid; mp: 233–234° C. Mass spectrum (ESI, [M+H]⁺) m/z 454. $^1$H NMR (400 MHz, DMSO-$d_6$) δ 7.59–7.56 (m, 2H), 7.47 (d, 1H, J=7.33 Hz), 7.39 (t, 2H, J=7.33 Hz), 7.35–7.30 (m, 3H), 7.15 (d, 2H, J=8.40 Hz), 7.07 (dd, 1H, J=9.05 and 2.45 Hz), 5.87 (s, 2H), 5.42 (s, 2H), 5.16 (s, 2H), and 1.22 ppm (s, 9H).

Elemental Analysis for $C_{29}H_{27}NO_4$: Calculated: C, 76.80; H, 6.00; N, 3.09. Found: C, 76.55; H, 6.07; N, 2.98.

EXAMPLE 8

9-(4-tert-Butylbenzyl)-6-hydroxy-1,9-dihydropyrano[3,4-b]indole-3,4-dione

Step 1

Ethyl 1-(4-tert-butylbenzyl)-5-methoxy-1H-indole-2-carboxylate

The title compound was prepared from ethyl 5-methoxy-1H-indole-2-Carboxylate and 4-(tert-butyl) benzyl bromide in substantially the same manner, as described in step 1 of Example 1. The product was obtained as a solid. Mass spectrum (ESI, [M−H]⁻) m/z 364. $^1$H NMR (400 MHz, DMSO-$d_6$) δ 7.48 (d, 1H, J=9.20 Hz), 7.27 (s, 1H), 7.24 (d, 2H, J=7.18 Hz), 7.16 (d, 1H, J=2.44 Hz), 6.96–6.92 (m, 3H), 5.77 (s, 2H), 4.28 (q, 2H), 3.76 (s, 3H), 1.28 (s, 3H), and 1.20 ppm (s, 9H).

Elemental Analysis for $C_{23}H_{27}NO_3$: Calculated: C, 75.59; H, 7.45; N, 3.83. Found: C, 75.94; H, 7.67; N, 3.66.

Step 2

[1-(4-tert-Butylbenzyl)-5-methoxy-1H-indol-2-yl]methanol

The title compound was prepared from ethyl 1-(4-tert-butylbenzyl)-5-methoxy-1H-indole-2-Carboxylate and lithium aluminum hydride in substantially the same manner, as described in step 3 of Example 1. The product was obtained as an oil. Mass spectrum (ESI, [M−H]⁻) m/z 322. $^1$H NMR (400 MHz, DMSO-$d_6$) δ 7.27 (d, 2H, J=8.14 Hz), 7.20 (d, 1H, J=8.70 Hz), 7.01 (d, 1H, J=2.45 Hz), 6.94 (d, 2H, J=8.24 Hz), 6.68 (dd, 1H, J=8.85 and 2.44 Hz), 6.34 (s, 1H), 5.37 (s, 2H), 5.26 (t, 1H), 4.56 (d, 2H, J=4.43 Hz), 3.72 (s, 3H), and 1.21 ppm (s, 9H).

Step 3

[1-(4-tert-Butylbenzyl)-5-methoxy-1H-indol-2-yl] methyl acetate

The title compound was prepared from [1-(4-tert-butylbenzyl)-5-methoxy-1H-indol-2-yl]methanol and acetyl chloride in substantially the same manner, as described in step 4 of Example 1. The product was obtained as a white solid. Mass spectrum (ESI, [M+H]$^+$) m/z 366. $^1$H NMR (400 MHz, DMSO-d$_6$) δ 7.30 (s, 1H), 7.28 (d, 2H, J=8.10 Hz), 7.07 (d, 1H, J=2.45 Hz), 7.86 (d, 2H, J=8.24 Hz), 7.76 (dd, 1H, J=8.86 and 2.29 Hz), 6.54 (s, 1H), 5.36 (s, 2H), 5.18 (s, 2H), 3.74 (s, 3H), 1.77 (s, 3H), and 1.20 ppm (s, 9H).

Elemental Analysis for C$_{23}$H$_{27}$NO$_3$: Calculated: C, 75.59; H, 7.45; N, 3.83. Found: C, 75.37; H, 7.65; N, 3.70.

Step 4

[2-[(Acetyloxy)methyl]-1-(4-tert-butylbenzyl)-5-methoxy-1H-indol-3-yl](oxo)acetic acid

The title compound was prepared from [1-(4-tert-butylbenzyl)-5-methoxy-1H-indol-2-yl]methyl acetate and oxalyl chloride in substantially the same manner, as described in step 5 of Example 1. The product was obtained as a brown solid; mp: >105° C. (decomposed). Mass spectrum (ESI, [M−H]$^-$) m/z 436. $^1$H NMR (400 MHz, DMSO-d$_6$) δ 7.54 (d, 1H, J=8.10 Hz), 7.51 (d, 1H, J=1.68 Hz), 7.32 (d, 2H, J=8.25 Hz), 6.97–6.94 (m, 3H), 5.56 (s, 2H), 5.46 (s, 2H), 3.78 (s, 3H), 1.75 (s, 3H), and 1.21 ppm (s, 9H).

Elemental Analysis for C$_{25}$H$_{27}$NO$_6$·0.12 H$_2$O: Calculated: C, 68.3; H, 6.25; N, 3.19. Found: C, 69.00; H, 6.66; N, 2.99.

Step 5

9-(4-tert-Butylbenzyl)-6-methoxy-1,9-dihydropyrano[3,4-b]indole-3,4-dione

The title compound was prepared from [2-[(acetyloxy)methyl]-1-(4-tert-butylbenzyl)-5-methoxy-1H-indol-3-yl](oxo)acetic acid and aqueous potassium hydroxide in substantially the same manner as described in step 6 of Example 1, followed by the treatment with aq HCl in substantially the same manner as described in step 7 of Example 1. The product was obtained as an off-white solid; mp: 238–239° C. Mass spectrum (ESI, [M−H]$^-$) m/z 376. $^1$H NMR (400 MHz, DMSO-d$_6$) δ 7.56 (d, 1H, J=9.01 Hz), 7.48 (d, 1H, J=2.45 Hz), 7.35 (d, 2H, J=8.40 Hz), 7.14 (d, 2H, J=8.25 Hz), 6.98 (dd, 1H, J=8.86 and 2.44 Hz), 5.87 (s, 2H), 5.42 (s, 2H), 3.81 (s, 3H), 1.22 ppm (s, 9H).

Elemental Analysis for C$_{23}$H$_{23}$NO$_4$: Calculated: C, 73.19; H, 6.14; N, 3.71. Found: C, 73.23; H, 6.11; N, 3.60.

Step 6

9-(4-tert-Butylbenzyl)-6-hydroxy-1,9-dihydropyrano[3,4-b]indole-3,4-dione

Boron tribromide (2.2 mL, 23.3 mmol) was added dropwise to a stirring suspension of 9-(4-tert-Butylbenzyl)-6-methoxy-1,9-dihydropyrano[3,4-b]indole-3,4-dione (4.92 g, 13.0 mmol) in methylene chloride (25 mL) at −78° C. under a nitrogen atmosphere over a period of 20 minutes. The mixture was then warmed up to room temperature. After stirring at room temperature for 6.5 hours, the reaction mixture was carefully quenched with a small amount of water and the evaporated to dryness. The residue was stirred in ether and filtered to afford a brown solid. Crystallization from aqueous methanol afforded the title compound as a brown solid (1.72 g). Mass spectrum (ESI, [M−H]$^-$) m/z 362. $^1$HNMR (400 MHz, DMSO-d$_6$): δ 9.39 (s, 1H), 7.44 (d, 1H, J=8.85 Hz), 7.40 (d, 1H, J=2.29 Hz), 7.34 (d, 2H, J=8.25 Hz), 6.80 (dd, 1H, J=8.86 and 2.29 Hz), 5.84 (s, 2H), 5.37 (s, 2H), 1.22 ppm (s, 9H).

Elemental Analysis for C$_{22}$H$_{21}$NO$_4$·0.7 H$_2$O: Calculated: C, 70.27; H, 6.00; N, 3.73. Found: C, 70.01; H, 5.62; N, 3.81.

EXAMPLE 9

9-Benzyl-6-(4-chlorophenyl)-1,9-dihydropyrano[3,4-b]indole-3,4-dione

Step 1

(1-Benzyl-5-bromo-1H-indol-2-yl)methanol

The title compound was prepared from ethyl 5-bromo-1-benzyl-1H-indole-2-carboxylate and lithium aluminum hydride in substantially the same manner, as described in step 3 of Example 1. The product was obtained as a semi-solid. Mass spectrum (ESI, [M−H]$^-$) m/z 314. $^1$H NMR (400 MHz, DMSO-d$_6$) δ 7.67 (s, 1H), 7.58–7.15 (m, 4H), 7.12 (d, 1H, J=8.69 and 1.97 Hz), 6.98 (d, 2H, J=8.34 Hz), 6.41 (s, 1H), 5.43 (s, 2H), 5.33 (t, 1H, J=5.57 Hz), and 4.54 ppm (d, 2H, J=5.43 Hz).

Step 2

(1-Benzyl-5-bromo-1H-indol-2-yl)methyl acetate

The title compound was prepared from (1-benzyl-5-bromo-1H-indol-2-yl)methanol and acetyl chloride in substantially the same manner, as described in step 4 of Example 1. The product was obtained as a semi-solid. Mass spectrum (ESI, [M−H]$^-$) m/z 356. $^1$H NMR (400 MHz, DMSO-d$_6$) δ 7.78 (d, 1H, J=2.13 Hz), 7.38 (d, 1H, J=8.86 Hz), 7.29–7.20 (m, 4H), 6.94 (d, 2H, J=7.17 Hz), 6.64 (s, 1H), 5.47 (s, 2H), 5.21 (s, 2H), and 1.79 ppm (s, 3H).

Step 3

[1-Benzyl-5-bromo-2-(hydroxymethyl)-1H-indol-3-yl](oxo)acetic acid, potassium salt

Oxalyl chloride (30.2 mL) was added dropwise to a stirring solution of (1-benzyl-5-bromo-1H-indol-2-yl)methyl acetate (31.5 g, 88.0 mmol) in THF (890 mL) at room temperature over a period of 30 minutes under a nitrogen atmosphere. The reaction was monitored by TLC. More oxalyl chloride was added as needed. After the reaction completed, the reaction mixture was quenched carefully with water and extracted with ethyl acetate. The organic extracts were washed with water, and brine, dried over anhydrous magnesium sulfate, and evaporated to give a solid. This solid was treated with aqueous potassium hydroxide (2.0 N, 96.8 mL, 193.6 mmol) in THF:MeOH (1:1, 800 mL) with stirring at room temperature for 2 h. The mixture was concentrated to yield a semi-solid. Trituration with water and collection of the solid by filtration afforded the title compound as a light brown solid (32.2 g), mp: >160° C. (dec); Mass spectrum (ESI, [M−H]$^-$) m/z 386. $^1$H NMR (400 MHz, DMSO-$d_6$) δ 8.35 (d, 1H, J=1.99 Hz), 7.40 (d, 1H, J=8.70 Hz), 7.29–7.26 (m, 4H), 7.23 (d, 2H, J=7.33 Hz), 7.10 (d, 2H, J=7.18 Hz), 5.72 (b, 1H), 5.59 (s, 2H), and 4.81 ppm (s, 2H).

Elemental Analysis for $C_{18}H_{13}BrNO_4 \cdot 1.0$ K $\cdot 1.0$ $H_2O$: Calculated: C, 48.66; H, 3.40; N, 3.15. Found: C, 48.61; H, 3.36; N, 2.89.

Step 4

9-Benzyl-6-(4-chlorophenyl)-1,9-dihydropyrano[3,4-b]indole-3,4-dione

A mixture of [1-benzyl-5-bromo-2-(hydroxymethyl)-1H-indol-3-yl](oxo)acetic acid, potassium salt (3.15 g, 7.4 mmol), 4-Chlorophenylboronic acid (1.74 g, 2.6 mmol), potassium carbonate (2.55 g, 13.7 mmol), palladium(II) acetate (0.032 g) and tetrabutylammonium bromide (2.4 g, 7.4 mmol) in 15% dioxane in water (45 mL) was stirred at 70° C. The reaction was monitored by TLC. After no [1-benzyl-5-bromo-2-(hydroxymethyl)-1H-indol-3-yl](oxo) acetic acid, was detected by TLC, the reaction was cooled down and solvent was decanted. The dark gum-like oil was partitioned between ethyl acetate and 10% aqueous HCl. The upper organic layer was separated, washed with water, and filtered. This filtrate was evaporated to give a solid. This solid was triturated with ethyl ether with stirring and dried in vacuum at 60° C. for 8 hours. to afford the title compound as an off-white solid (0.77 g), m.p. 263–264° C. Mass spectrum (ESI, [M+H]$^+$) m/z 402. $^1$H NMR (400 MHz, DMSO-$d_6$) δ 8.19 (s, 1H), 7.71–7.67 (m, 3H), 7.63 (dd, 1H, J=8.66 and 1.83 Hz),), 7.49 (dd, 2H, J=8.54 and 1.95 Hz), 7.34–7.25 (m, 3H), 7.22 (d, 2H, J=7.46 Hz), 5.88 (s, 2H), and 5.52 ppm (s, 2H).

Elemental Analysis for $C_{24}H_{16}ClNO_3 \cdot 0.4$ $H_2O$: Calculated: C, 70.47; H, 4.14; N, 3.42. Found: C, 70.57; H, 4.19; N, 3.12.

EXAMPLE 10

[1-Benzyl-5-(4-Chlorophenyl)-2-(hydroxymethyl)-1H-indol-3-yl](oxo)acetic acid, potassium salt

Step 1

[1-Benzyl-5-(4-chlorophenyl)-2-(hydroxymethyl)-1H-indol-3-yl](oxo)acetic acid, potassium salt A solution of 9-benzyl-6-(4-chlorophenyl)-1,9-dihydropyrano[3,4-b]indole-3,4-dione (0.613 g, 0.1.53 mmol) and (1.0 N, 1.6 mL, 1.6 mmol) in THF:MeOH (1:1, 14 mL) was stirred at room temperature for 2 hours. The reaction was followed by NMR. More aqueous potassium hydroxide was added as needed. After no starting material was detected, the reaction mixture was evaporated to dryness. The residual solid was triturated with ethyl ether to afford the title compound as a light grey solid, mp: 225–226° C.; Mass spectrum (ESI, [M–H]$^-$) m/z 418. $^1$H NMR (400 MHz, DMSO-$d_6$) δ 8.51 (s, 1H), 7.64 (d, 2H, J=8.55 Hz), 7.52–7.49 (m, 3H), 7.45 (d, 1H, J=8.55 Hz), 7.31–7.28 (m, 2H), 7.18 (d, 1H, J=7.64 Hz), 7.15 (d, 2H, J=7.64 Hz), 5.75 (t, 1H, J=7.57 Hz),), 5.61 (s, 2H), and 4.81 ppm (d, 2H, J=5.95 Hz).

Elemental Analysis for $C_{24}H_{17}ClNO_4 \cdot 1.0$ K $\cdot 1.6$ $H_2O$: Calculated: C, 59.22; H, 4.18; N, 2.88. Found: C, 59.02; H, 3.90; N, 2.70.

EXAMPLE 11

9-Benzyl-6-(3-methylphenyl)-1,9-dihydropyrano[3,4-b]indole-3,4-dione

Step 1

9-Benzyl-6-(3-methylphenyl)-1,9-dihydropyrano[3,4-b]indole-3,4-dione

The title compound was prepared from [1-benzyl-5-bromo-2-(hydroxymethyl)-1H-indol-3-yl](oxo)acetic acid, potassium salt and m-tolylboronic acid in substantially the same manner, as described in step 4 of Example 9. The product was obtained as a grey solid, mp: 225–226° C.; Mass spectrum (ESI, [M+H]$^+$) m/z 382. $^1$H NMR (400 MHz, DMSO-$d_6$) δ 8.22 (s, 1H), 7.22 (d, 1H, J=8.40 Hz), 7.65 (dd, 1H, J=8.45 and 1.83 Hz), 7.49 (s, 1H), 7.47–7.34 (m, 3H), 7.31 (d, 1H, J=7.33 Hz), 7.27 (d, 2H, J=8.40 Hz), 7.18 (d, 1H, J=7.48 Hz), 5.92 (s, 2H), 5.55 (s, 2H), and 2.39 ppm (s, 3H).

Elemental Analysis for $C_{25}H_{19}NO_3 \cdot 0.4$ $H_2O$: Calculated: C, 77.26; H, 5.14; N, 3.60. Found: C, 77.45; H, 5.09; N, 3.51.

EXAMPLE 12

9-Benzyl-6-(1,1'-biphenyl-4-yl)-1,9-dihydropyrano[3,4-b]indole-3,4-dione

Step 1

9-Benzyl-6-(1,1'-biphenyl-4-yl)-1,9-dihydropyrano[3,4-b]indole-3,4-dione

The title compound was prepared from [1-benzyl-5-bromo-2-(hydroxymethyl)-1H-indol-3-yl](oxo)acetic acid, potassium salt and 4-biphenylboronic acid in substantially the same manner, as described in step 4 of Example 9. The product was obtained as a white solid, mp: 254–255° C.; Mass spectrum (ESI, [M+H]$^+$) m/z 444. $^1$H NMR (400 MHz, DMSO-$d_6$) δ 8.26(s, 1H), 7.75–7.68 (m, 8H), 7.45–7.43 (m, 2H), 7.36–7.23 (m, 6H), 5.89 (s, 2H), 5.53 ppm (s, 2H).

Elemental Analysis for $C_{30}H_{21}NO_3 \cdot 0.2$ $H_2O$: Calculated: C, 80.59; H, 4.82; N, 3.13. Found: C, 80.70; H, 4.60; N, 2.82.

EXAMPLE 13

[1-Benzyl-5-(1,1'-biphenyl-4-yl)-2-(hydroxymethyl)-1H-indol-3-yl](oxo)acetic acid, potassium salt

Step 1

[1-Benzyl-5-(1,1'-biphenyl4-yl)-2-(hydroxymethyl)-1H-indol-3-yl](oxo)acetic acid, potassium salt The title compound was prepared from 9-benzyl-6-(1,1'-biphenyl-4-yl)-1,9-dihydropyrano[3,4-b]indole-3,4-dione and aqueous potassium hydroxide in substantially the same manner, as described in step 1 of Example 10. The product was obtained as a light yellow solid, mp: 266–268° C.; Mass spectrum (ESI, [M–H]$^-$) m/z 460. $^1$H NMR (400 MHz, DMSO-$d_6$) δ 8.58 (s, 1H), 7.70–7.72 (m, 6H), 7.52 (s, 2H), 7.48 (t, 2H, J=7.63 Hz), 7.36 (t, 1H, J=7.33 Hz), 7.32–7.29

(m, 2H),), 7.24 (t, 1H, J=7.02 Hz), 7.17 (d, 1H, J=7.63 Hz), 5.76 (t, 1H), 5.62 (s, 2H), and 4.83 ppm (d, 2H, J=5.34 Hz).

Elemental Analysis for $C_{30}H_{23}NO_4 \cdot 1.0$ K$\cdot 1.50$ H$_2$O: Calculated: C, 68.42; H, 4.79; N, 2.66. Found: C, 68.24; H, 4.85; N, 2.46.

What is claimed:

1. A compound of formula I:

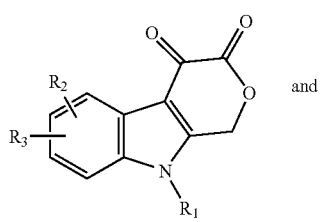

(I)

and

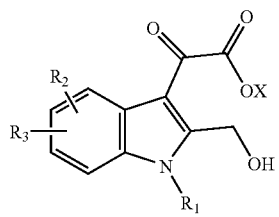

(II)

wherein:

R$_1$ is C$_1$–C$_8$ alkyl, C$_3$–C$_6$ cycloalkyl, —CH$_2$—C$_3$–C$_6$ cycloalkyl, pyridinyl, —CH$_2$-pyridinyl, phenyl or benzyl, wherein the rings of the cycloalkyl, pyridinyl, phenyl and benzyl groups may be optionally substituted by from 1 to 3 groups selected from halogen, C$_1$–C$_6$ alkyl, C$_1$–C$_6$ perfluoroalkyl, —O—C$_1$–C$_6$ perfluoroalkyl, C$_1$–C$_6$ alkoxy, —OH, —NH$_2$, or —NO$_2$;

R$_2$ is hydrogen, halogen, C$_1$–C$_6$ alkyl, C$_1$–C$_3$ perfluoroalkyl, C$_1$–C$_6$ alkoxy, C$_3$–C$_6$ cycloalkyl, —CH$_2$—C$_3$–C$_6$ cycloalkyl, hydroxy, —NH$_2$, or —NO$_2$;

R$_3$ is hydrogen, halogen, C$_1$–C$_6$ alkyl, C$_1$–C$_3$ perfluoroalkyl, C$_1$–C$_6$ alkoxy, C$_3$–C$_6$ cycloalkyl, —CH$_2$—C$_3$–C$_6$ cycloalkyl, hydroxy, —NH$_2$, —NO$_2$, phenyl, benzyl, benzyloxy, pyridinyl, or —CH$_2$-pyridinyl, wherein the rings of these groups may be optionally substituted by from 1 to 3 groups selected from phenyl, halogen, C$_1$–C$_6$ alkyl, C$_1$–C$_6$ perfluoroalkyl, —O—C$_1$–C$_6$ perfluoroalkyl, C$_1$–C$_6$ alkoxy, —OH, —NH$_2$, or —NO$_2$; or a pharmaceutically acceptable salt or ester form thereof.

2. A compound of claim 1 that is of formula III:

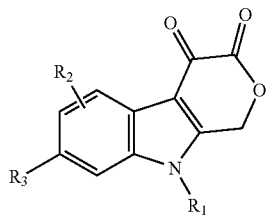

(III)

wherein:

R$_1$ is C$_1$–C$_8$ alkyl, C$_3$–C$_6$ cycloalkyl, —CH$_2$—C$_3$–C$_6$ cycloalkyl, pyridinyl, —CH$_2$-pyridinyl, phenyl or benzyl, wherein the rings of the cycloalkyl, pyridinyl, phenyl and benzyl groups may be optionally substituted by from 1 to 3 groups selected from halogen, C$_1$–C$_6$ alkyl, C$_1$–C$_6$ perfluoroalkyl, —O—C$_1$–C$_6$ perfluoroalkyl, C$_1$–C$_6$ alkoxy, —OH, —NH$_2$, or —NO$_2$;

R$_2$ is hydrogen, halogen, C$_1$–C$_6$ alkyl, C$_1$–C$_3$ perfluoroalkyl, C$_1$–C$_6$ alkoxy, C$_3$–C$_6$ cycloalkyl, —CH$_2$—C$_3$–C$_6$ cycloalkyl, —NH$_2$, or —NO$_2$;

R$_3$ is hydrogen, halogen, C$_1$–C$_6$ alkyl, C$_1$–C$_3$ perfluoroalkyl, C$_1$–C$_6$ alkoxy, C$_3$–C$_6$ cycloalkyl, —CH$_2$—C$_3$–C$_6$ cycloalkyl, hydroxy, —NH$_2$, —NO$_2$, phenyl, benzyl, benzyloxy, pyridinyl, or —CH$_2$-pyridinyl, wherein the rings of these groups may be optionally substituted by from 1 to 3 groups selected from halogen, C$_1$–C$_6$ alkyl, C$_1$–C$_6$ perfluoroalkyl, —O—C$_1$–C$_6$ perfluoroalkyl, C$_1$–C$_6$ alkoxy, —OH, —NH$_2$, or —NO$_2$; or a pharmaceutically acceptable salt or ester form thereof.

3. A compound of claim 1 that is of formula (IV)

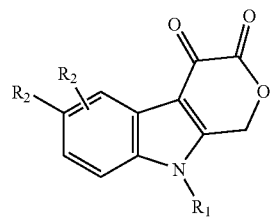

(IV)

wherein:

R$_1$ is C$_1$–C$_8$ alkyl, C$_3$–C$_6$ cycloalkyl, —CH$_2$—C$_3$–C$_6$ cycloalkyl, pyridinyl, —CH$_2$-pyridinyl, phenyl or benzyl, wherein the rings of the cycloalkyl, pyridinyl, phenyl and benzyl groups may be optionally substituted by from 1 to 3 groups selected from halogen, C$_1$–C$_6$ alkyl, C$_1$–C$_6$ perfluoroalkyl, —O—C$_1$–C$_6$ perfluoroalkyl, C$_1$–C$_6$ alkoxy, —OH, —NH$_2$, or —NO$_2$;

R$_2$ is hydrogen, halogen, C$_1$–C$_6$ alkyl, C$_1$–C$_3$ perfluoroalkyl, C$_1$–C$_6$ alkoxy, C$_3$–C$_6$ cycloalkyl, —CH$_2$—C$_3$–C$_6$ cycloalkyl, —NH$_2$, or —NO$_2$;

R$_3$ phenyl, benzyl, benzyloxy, pyridinyl, or —CH$_2$-pyridinyl, with the rings of these groups being optionally substituted by from 1 to 3 groups selected from halogen, C$_1$–C$_3$ alkyl, C$_1$–C$_3$ perfluoroalkyl, —O—C$_1$–C$_3$ perfluoroalkyl, C$_1$–C$_3$ alkoxy, —OH, —NH$_2$, or —NO$_2$; or a pharmaceutically acceptable salt or ester form thereof.

4. A compound of claim 1 that is of formula (V):

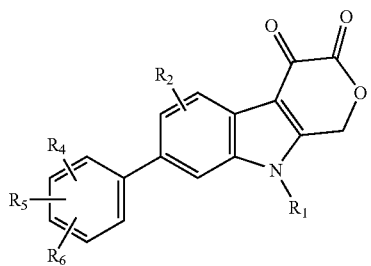

(V)

wherein:

R$_1$ is C$_1$–C$_8$ alkyl, preferably C$_1$–C$_6$ alkyl, C$_3$–C$_6$ cycloalkyl, —CH$_2$—C$_3$–C$_6$ cycloalkyl, or benzyl, wherein the rings of the cycloalkyl and benzyl groups may be optionally substituted by from 1 to 3 groups selected from halogen, $C_1$–$C_6$ alkyl, $C_1$–$C_6$ perfluoroalkyl, —O—$C_1$–$C_6$ perfluoroalkyl, $C_1$–$C_6$ alkoxy, —OH, —NH$_2$, or —NO$_2$;

$R_2$ is hydrogen, halogen, $C_1$–$C_6$ alkyl, $C_1$–$C_3$ perfluoroalkyl, preferably —CF$_3$, $C_1$–$C_6$ alkoxy, $C_3$–$C_6$ cycloalkyl, —CH$_2$—$C_3$–$C_6$ cycloalkyl, hydroxy, —NH$_2$, or —NO$_2$;

$R_4$, $R_5$ and $R_6$ are each independently hydrogen, phenyl, halogen, $C_1$–$C_3$ alkyl, $C_1$–$C_3$ perfluoroalkyl, —O—$C_1$–$C_3$ perfluoroalkyl, $C_1$–$C_3$ alkoxy, —OH, —NH$_2$, or —NO$_2$; or a pharmaceutically acceptable salt or ester form thereof.

5. A compound of claim 1 that is of formula VI:

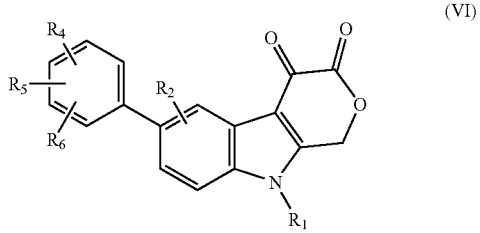

(VI)

wherein:

$R_1$ is $C_1$–$C_8$ alkyl, $C_3$–$C_6$ cycloalkyl, —CH$_2$—$C_3$–$C_6$ cycloalkyl, or benzyl, wherein the rings of the cycloalkyl and benzyl groups may be optionally substituted by from 1 to 3 groups selected from halogen, $C_1$–$C_6$ alkyl, $C_1$–$C_6$ perfluoroalkyl, preferably —CF$_3$, —O—$C_1$–$C_6$ perfluoroalkyl, preferably —O—CF$_3$, $C_1$–$C_6$ alkoxy, —OH, —NH$_2$, or —NO$_2$;

$R_2$ is hydrogen, halogen, $C_1$–$C_6$ alkyl, $C_1$–$C_3$ perfluoroalkyl, preferably —CF$_3$, $C_1$–$C_6$ alkoxy, $C_3$–$C_6$ cycloalkyl, —CH$_2$—$C_3$–$C_6$ cycloalkyl, hydroxy, —NH$_2$, or —NO$_2$; and $R_4$, $R_5$ and $R_6$ are each independently hydrogen, halogen, $C_1$–$C_3$ alkyl, $C_1$–$C_3$ perfluoroalkyl, preferably —CF$_3$, —O—$C_1$–$C_3$ perfluoroalkyl, preferably —O—CF$_3$, $C_1$–$C_3$ alkoxy, —OH, —NH$_2$, or —NO$_2$; or a pharmaceutically acceptable salt or ester form thereof.

6. The compound of claim 1 which is 9-(4-Methylbenzyl)-6-[4-(trifluoromethoxy)phenyl]-1,9-dihydropyrano[3,4-b]indole-3,4-dione or a pharmaceutically acceptable salt or ester form thereof.

7. The compound of claim 1 which is 9-Benzyl-6-[4-(trifluoromethoxy)phenyl]-1,9-dihydropyrano[3,4-b]indole-3,4-dione or a pharmaceutically acceptable salt or ester form thereof.

8. The compound of claim 1 which is 9-(4-Methylbenzyl)-6-(3-Methylphenyl)-1,9-dihydropyrano[3,4-b]indole-3,3-dione or a pharmaceutically acceptable salt or ester form thereof.

9. The compound of claim 1 which is 9-(4-tert-butylbenzyl)-6-(3-Methylphenyl)-1,9-dihydropyrano[3,4-b]indole-3,4-dione or a pharmaceutically acceptable salt or ester form thereof.

10. The compound of claim 1 which is 6-(Benzyloxy)-9-(4-methylbenzyl)-1,9-dihydropyrano[3,4-b]indole-3,4-dione or a pharmaceutically acceptable salt or ester form thereof.

11. The compound of claim 1 which is 6-(Benzyloxy)-1,9-dihydropyrano[3,4-b]indole-3,4-dione or a pharmaceutically acceptable salt or ester form thereof.

12. The compound of claim 1 which is 6-(Benzyloxy)-9-(4-tertbutylbenzyl)-1,9-dihydropyrano[3,4-b]indole-3,4-dione or a pharmaceutically acceptable salt or ester form thereof.

13. The compound of claim 1 which is 9-(4-tertbutybenzyl)-6-hydroxy-1,9-dihydropyrano[3,4-b]indole-3,4-dione or a pharmaceutically acceptable salt or ester form thereof.

14. The compound of claim 1 which is 9-benzyl-6-(4-Chlorophenyl)-1,9-dihydropyrano[3,4-b]indole-3,4-dione or a pharmaceutically acceptable salt or ester form thereof.

15. The compound of claim 1 which is 9-benzyl-6-(3-Methylphenyl)-1,9-dihydropyrano[3,4-b]indole-3,4-dione or a pharmaceutically acceptable salt or ester form thereof.

16. The compound of claim 1 which is 9-benzyl-6-(1-1-bi-phenyl-4-yl)-1,9-dihydropyrano[3,4-b]indole-3,4-dione or a pharmaceutically acceptable salt or ester form thereof.

17. A pharmaceutical composition comprising a compound of claim 1 and a pharmaceutical carrier.

18. A method for treatment of thrombosis or fibrinolytic impairment in a mammal, the method comprising administering to a mammal in need thereof a pharmaceutically effective amount of a compound of claim 1.

19. A method of claim 18 wherein the thrombosis or fibrinolytic impairment is associated with formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery or peripheral arterial occlusion.

* * * * *

UNITED STATES PATENT AND TRADEMARK OFFICE
CERTIFICATE OF CORRECTION

PATENT NO. : 7,101,903 B2 Page 1 of 1
APPLICATION NO. : 10/731290
DATED : September 5, 2006
INVENTOR(S) : Hassan Elokdah et al.

It is certified that error appears in the above-identified patent and that said Letters Patent is hereby corrected as shown below:

Title Page,
Item (54) Title:
Delete "INHIBITIORS" and insert -- INHIBITORS --.

Signed and Sealed this

Twenty-fifth Day of September, 2007

JON W. DUDAS
*Director of the United States Patent and Trademark Office*

UNITED STATES PATENT AND TRADEMARK OFFICE
CERTIFICATE OF CORRECTION

PATENT NO. : 7,101,903 B2  Page 1 of 1
APPLICATION NO. : 10/731290
DATED : September 5, 2006
INVENTOR(S) : Hassan Elokdah et al.

It is certified that error appears in the above-identified patent and that said Letters Patent is hereby corrected as shown below:

Column 29, claim 1: Lines 20-27
Delete the structure depicted and "(II)"

" 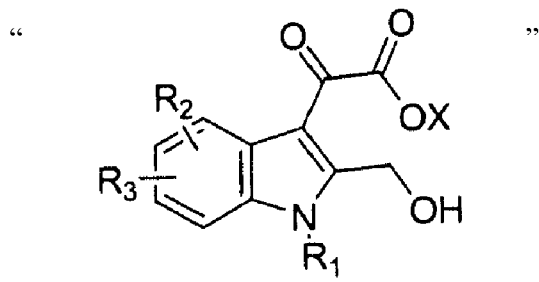 "

and "(II)"

Signed and Sealed this

Ninth Day of September, 2008

JON W. DUDAS
*Director of the United States Patent and Trademark Office*